US006221591B1

(12) United States Patent
Aerts

(10) Patent No.: US 6,221,591 B1
(45) Date of Patent: Apr. 24, 2001

(54) DETERMINATION OF A GENETIC RISK FACTOR FOR INFECTION AND OTHER DISEASES, AND DETECTION OF ACTIVATED PHAGOCYTES

(75) Inventor: J. M. F. G. Aerts, Abcoude (NL)

(73) Assignee: Universiteit Van Amsterdam, Amsterdam (NL)

(*) Notice: Subject to any disclaimer, the term of this patent is extended or adjusted under 35 U.S.C. 154(b) by 0 days.

(21) Appl. No.: 09/156,856

(22) Filed: Sep. 18, 1998

Related U.S. Application Data

(63) Continuation-in-part of application No. 08/486,839, filed on Jun. 7, 1995, now Pat. No. 5,928,928.

(51) Int. Cl.[7] .............................. C12Q 1/68; C07H 21/02; C07H 21/04; C12N 15/00; C12N 9/26
(52) U.S. Cl. .............................. 435/6; 536/23.1; 536/24.3; 985/76; 985/77; 985/78; 435/201
(58) Field of Search ....................... 435/6, 201; 556/23.1, 556/24.3; 530/350; 935/76, 77, 78

(56) References Cited

U.S. PATENT DOCUMENTS

| 5,811,535 | * | 9/1998 | Adamou et al. | 536/23.5 |
| 5,843,449 | * | 12/1998 | Boots et al. | 424/185.1 |
| 5,928,928 | * | 7/1999 | Aerts | 435/201 |

OTHER PUBLICATIONS

Boot et al., The Journal of Biological Chemistry 270 (44) : 26252–26256 (Nov. 1995).
Renkema et al., The Journal of Biological Chemistry 270 (5) : 2198–2202 (Feb. 1995).
Hakala et al., The Journal of Biological Chemistry 268 (34) : 25803–25810 (Dec. 1993).
Kramer et al., *Insect Biochemistry and Molecular Biology* 23(6) : 691–701 (1993). Abstract only.
1988 Stratagene Catalog, p. 39 (1988).

* cited by examiner

*Primary Examiner*—Ethan Whisenant
(74) *Attorney, Agent, or Firm*—Hoffman & Baron, LLP

(57) ABSTRACT

It is shown that a defect in the chitotriosidase gene is a risk factor with respect to susceptibility for infectious diseases with chitin-containing pathogens and the development of (rheumatoid) arthritis. The molecular basis of the relatively common chitotriosidase deficiency is a 24 bp duplication in the chitotriosidase gene. A convenient method allowing analysis of chitotriosidase genotype and subsequent determination of increased risk has been developed. Chitotriosidase is shown to be selectively secreted by macrophages upon specific activation and excreted by neutrophils by release of specific granules upon an appropriate stimulus. It has been shown that the measurement of plasma chitotriosidase activity can be successfully used for diagnosis of specific disorders and monitoring of efficacy of therapeutic interventions, at least in combination with information on the chitotriosidase genotype status of an individual.

20 Claims, 19 Drawing Sheets

DETERMINATION OF A GENETIC RISK FACTOR FOR INFECTION AND OTHER DISEASES, AND DETECTION OF ACTIVATED PHAGOCYTES

RELATED PATENT APPLICATIONS

This patent application is a continuation-in-part of U.S. patent application Ser. No. 08/486,839 filed on Jun. 17, 1995 and now U.S. Pat. No. 5,928,928.

FIELD OF THE INVENTION

This invention is in the field of genotype analysis to determine the presence of a genetic risk factor with respect to susceptibility to infectious diseases in which pathogens having a chitin-containing coat are involved and other kinds of diseases, such as rheumatoid arthritis. This invention provides novel nucleic acid molecules which may be used in such genotype analysis and methods of genotype analysis using such novel nucleic acid molecules.

Furthermore, the subject invention is in the fields of diagnosis and detection of activated phagocytes in specific pathologies and changes therein during therapy.

BACKGROUND OF THE INVENTION

Gaucher disease is an inherited disorder characterized by the accumulation in tissues of glucosylceramide-laden macrophages ('Gaucher cells') as the result of a deficiency in the lysosomal enzyme glucocerebrosidase [1]. The presence of Gaucher cells is responsible for the common symptoms in Gaucher patients, such as hepatomegaly, splenomegaly, and skeletal deterioration [1].

The clinical manifestations in glucocerebrosidase-deficient individuals are very heterogeneous. Onset of clinical symptoms may occur at very young age, but the disorder may also remain virtually asymptomatic. Accurate prediction of disease severity and progression is not possible on the basis of the mutant glucocerebrosidase genotype of Gaucher patients.

During our search for sensitive markers for the presence of Gaucher cells, we discovered that in plasma of symptomatic patients chitotriosidase activity is markedly elevated [2]. Our present experience with more than 700 symptomatic Gaucher patients indicates that the average plasma chitotriosidase activity is about 1000-fold higher than the normal mean.

The discovery that activated storage macrophages are the source of the excessive plasma chitotriosidase in Gaucher patients, made us conceive that several disease conditions in which activated neutrophils and/or macrophages are involved might show detectable chitotriosidase abnormalities that can be exploited for diagnosis as well as for monitoring and optimalisation of therapeutic intervention. The feasibility and validity of this is illustrated by a number of examples, involving Gaucher disease, atherosclerosis, sarcoidosis, multiple sclerosis, arthritis and Crohn disease.

Copending U.S. patent application Ser. No. 08/486,839 describes our discovery that man contains a chitinase, named chitotriosidase, that fulfills a role in resistance against infections with chitin-containing pathogens by virtue of its ability to degrade chitin, an essential structural component of their coatings. Said patent application claims the use of chitotriosidase in therapy or prophylaxis against infectious diseases.

SUMMARY OF THE INVENTION

We herein describe the discovery of a novel genetic risk factor for infectious diseases, being an inherited abnormality in the chitotriosidase gene. A method that allows convenient analysis of chitotriosidase genotype is described.

Chitotriosidase genotype analysis is valuable in relation to prophylaxis of fungal infections and for the assessment of increased risk for other disease conditions such as (rheumatoid) arthritis. Information on the chitotriosidase genotype status also allows reliable interpretation of chitotriosidase enzyme activity levels.

Additionally, it is shown that chitotriosidase is a sensitive marker for monitoring activated phagocytes. It can be applied for diagnostic purposes as well as for monitoring efficacy of therapeutic intervention, in particular when also information about the chitotriosidase genotype of the examined individual is available. The value of chitotriosidase as marker for activated phagocytes is illustrated by a number of examples involving Gaucher disease, atherosclerosis, sarcoidosis, arthritis, multiple sclerosis, Crohn disease and neutrophil activation by G-CSF or GM-CSF administration.

Deficiency in chitotriosidase activity can be observed in specific individuals. About 5% of all subjects, including Gaucher patients, shows no true chitotriosidase activity due to the homozygous presence of a mutant chitotriosidase gene. About 35% of all individuals is carrier for this chitotriosidase defect. Chitotriosidase activity levels in materials (plasma, leukocytes, urine) of carriers are on average half those in control materials. Therefore, the interpretation of chitotriosidase activity levels without information on the chitotriosidase genotype of an individual is difficult. Consequently, there is a need for a convenient method that allows accurate identification of the chitotriosidase genotype.

Determination of the chitotriosidase genotype status of an individual is not only crucial for interpretation of enzyme activity levels in relation to diagnosis or monitoring of therapeutic intervention. Moreover, it is of great value for another reason. Infections with chitin-containing pathogens are a serious threat to mankind (for an extensive description see U.S. patent application Ser. No. 08/486,839). Most pathogens, with the exception of bacteria and viruses, have chitin as essential structural component in their coatings. It is known that chitinases in plants play an important role in defense against chitin-containing fungi [3]. Until recently it has generally been thought that vertebrates lack a similar defense mechanism. Our discovery that human phagocytes produce an analogous chitinase is therefore of importance.

Recombinant chitotriosidase has been found to be a potent inhibitor of hyphal growth of fungi like Candida and Aspergillus, and moreover it can protect mice against systemic infections with these pathogens. Systemic fungal infections are an increasing clinical problem for several reasons [4]. Firstly, the efficacy of the present treatment modalities is limited due to the development of resistance against antifungal agents and toxicity of the compounds. Secondly, the susceptibility for fungal infections is markedly increased when the immune system is suppressed. The number of individuals with a suppressed immune system increases (because of chemotherapy, transplantations, specific infections or genetic causes). Consequently, the incidence of systemic fungal infections, which are quite often lethal, has markedly increased in the last decade. There are indications that the genetic background may influence the susceptibility for infections. Most likely during immune suppression the resistance against pathogens heavily relies on innate defense mechanisms, of which chitotriosidase is one. It was conceived by us that a deficiency in chitotriosidase activity is an important risk factor with respect to susceptibility for chronic infection with and reduced resistance against chitin-containing pathogens, especially when the immune system is suppressed. About 5% of all subjects shows a deficiency in chitotriosidase activity, and is therefore at increased risk for particular infections. The elucidation of the genetic basis of inherited chitotriosidase deficiency allowed us to develop methods that sensitively detect carriers and homozygotes for the defect.

In conclusion, determination of the (hetero- or homoallelic) presence of a 24 bp duplication in the chitotriosidase gene allows convenient identification of individuals that are at increased risk for developing a chronic infection with chitin-containing pathogens. Especially in the case of suppression of the immune system, a prophylactic treatment with antifungal agents (including chitotriosidase, see patent application Ser. No. 08/486,839) should be considered for those individuals carrying the chitotriosidase defect.

Determination of the chitotriosidase genotype is also valuable to assess the risk for other disease conditions such as (rheumatoid) arthritis. Information on the chitotriosidase genotype of an individual is moreover essential to interpret data on chitotriosidase activity levels in tissues and plasma that are for instance collected for diagnostic reasons or for the assessment of efficacy of therapeutic intervention.

Exons (E1—E12) are defined on the basis of cloned cDNAs. The locations of restriction sites are indicated. The symbols H and B indicate the locations of HindIII and BamHI restriction sites within the gene.

Fluorescence in situ hybridization of human metaphase chromosomes with a genomic chitotriosidase clone showed that the chitotriosidase gene locus is 1q31–q32.

Figure 2A:
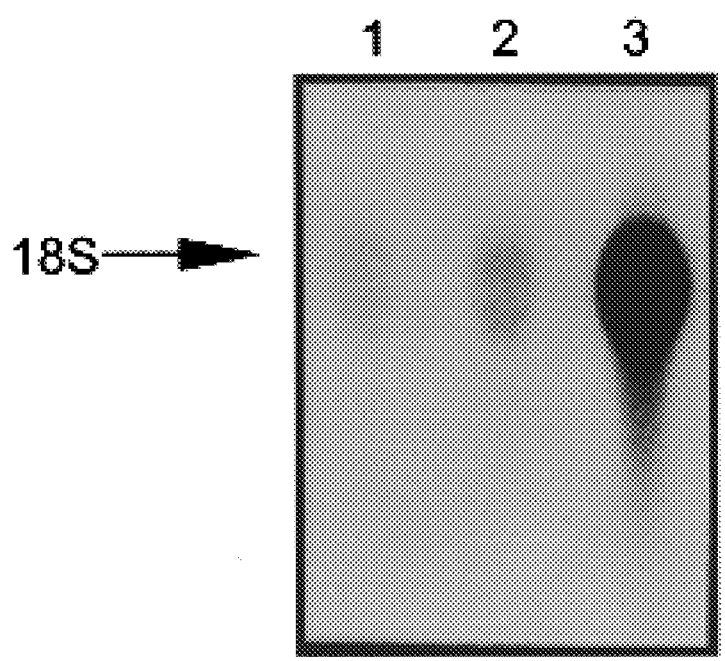
Figure 2B:
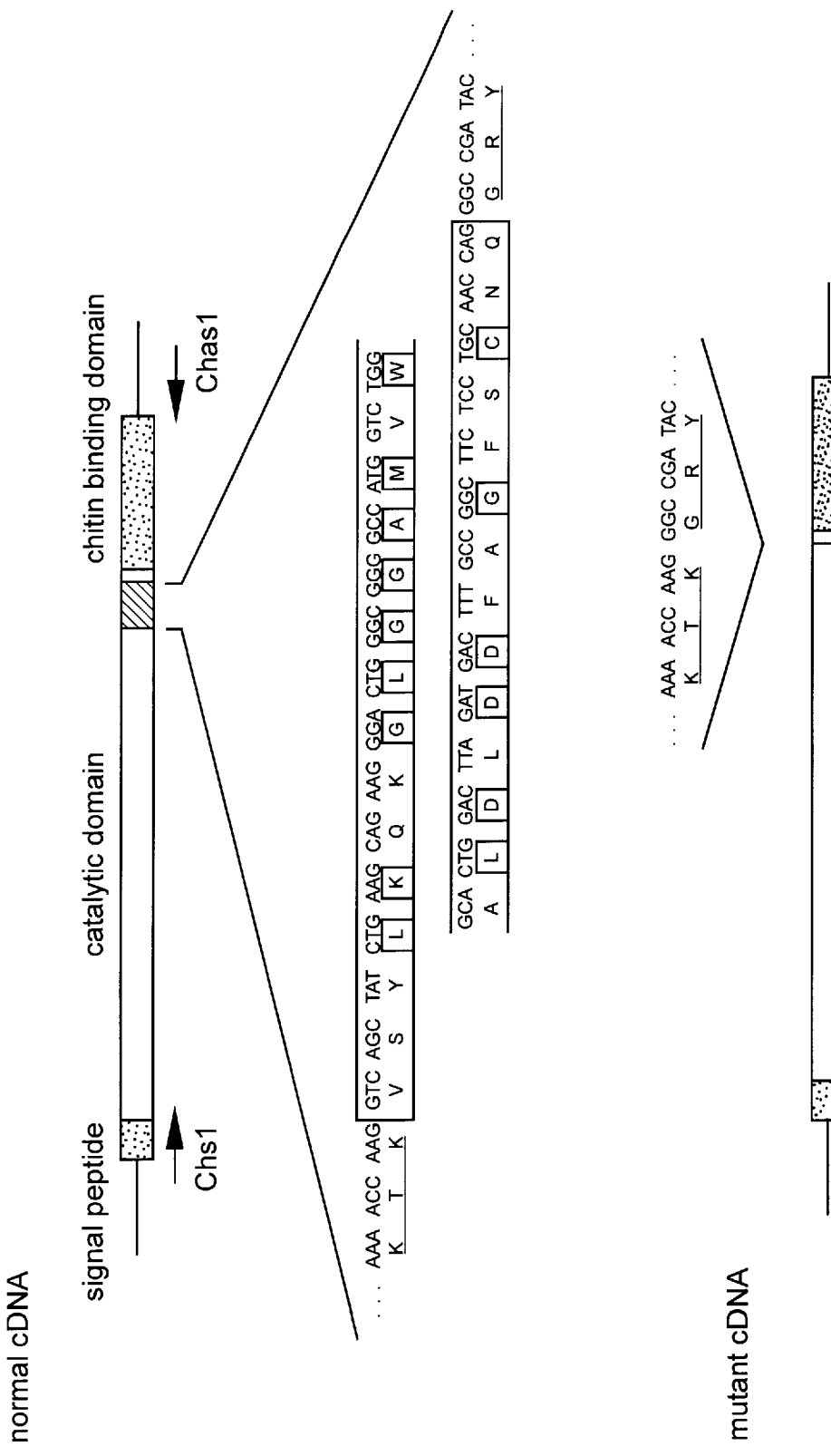

FIG. 2 shows the defect in chitotriosidase mRNA in deficient individuals.

Panel A: the detection of chitotriosidase mRNA in macrophages by Northern blot analysis. Lane 1: deficient individual; lane 2: deficient individual; lane 3: control individual.

Panel B: overview of normal and mutant chitotriosidase cDNA. The position of the signal peptide, the catalytic (TIM-barrel) domain and the chitin binding domain is shown. The arrows indicate the primers used to generate the complete coding sequence. The sequence of the deleted part in the mutant cDNA is depicted.

Figure 3A:
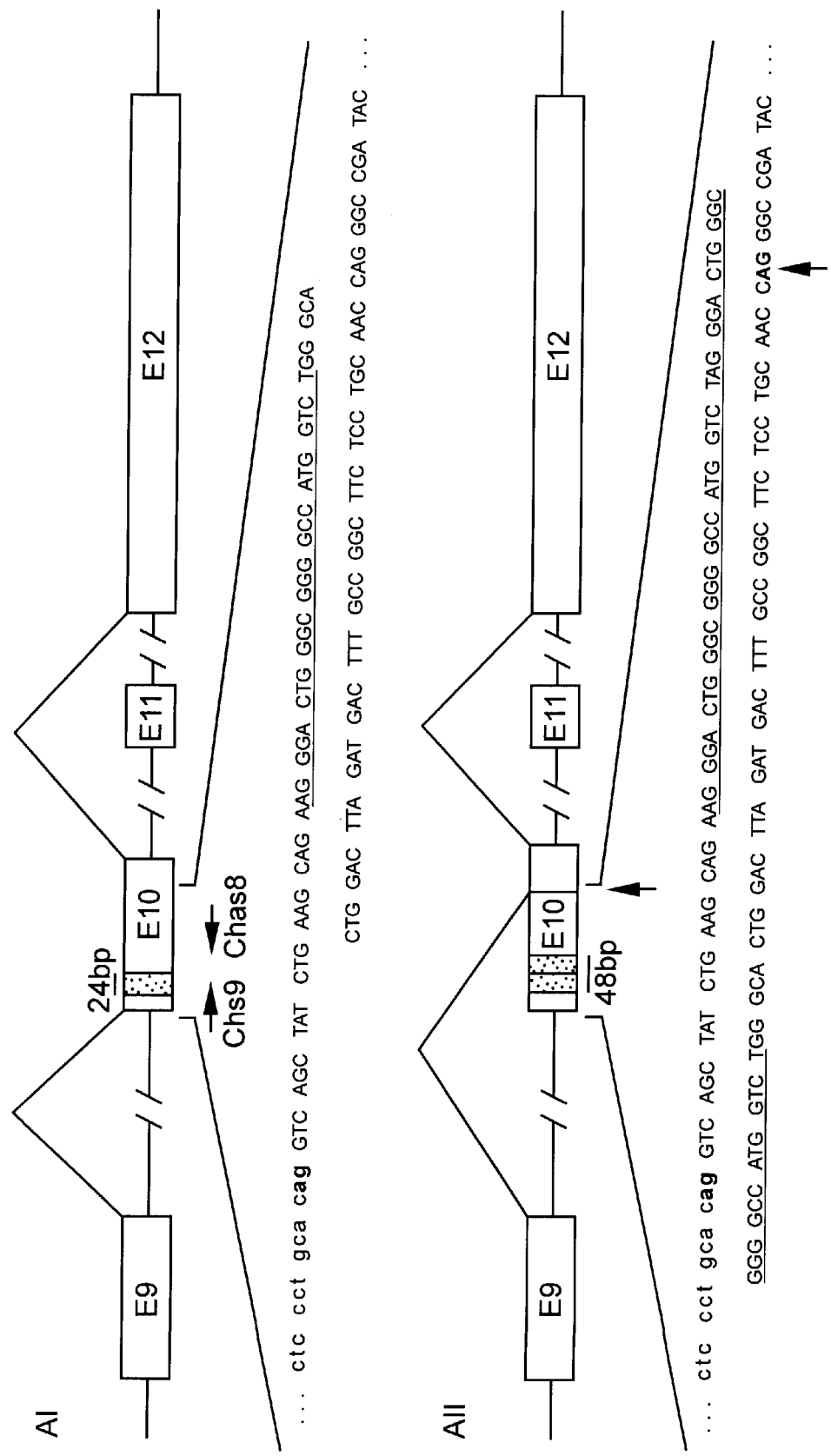
Figure 3B:
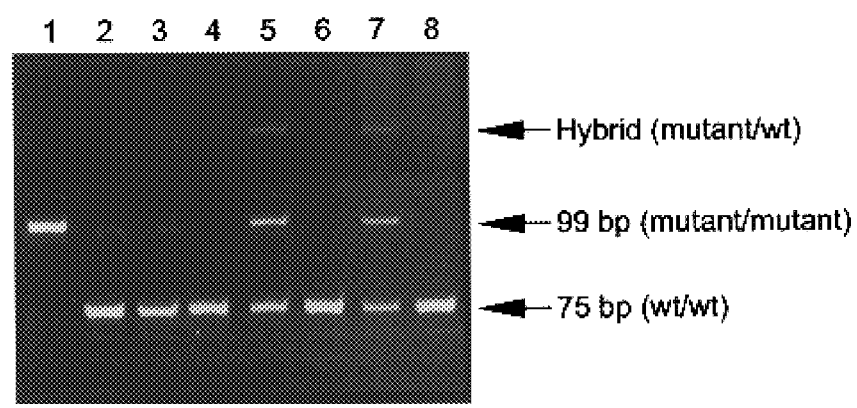

FIG. 3 shows the defect in the chitotriosidase gene in deficient individuals.

Panel A: overview of the relevant part of the chitotriosidase gene. The upper part (AI) shows the normal gene. The arrows indicate the primers used for amplification of the genomic DNA. The lines above the gene show the normal splicing in which exon 11 is skipped. The lower part (AII) shows the difference in the mutant gene. The mutant gene contains a 24 bp duplication in exon 10. Above the gene the difference in splicing is depicted. The arrow indicates the activated 3' splice site in the mutant gene.

Panel B: detection of the 24 bp duplication in the chitotriosidase gene by PCR of genomic DNA. Amplified fragments (primers Chs9 and Chas8) were separated on a native 10% polyacrylamide gel and stained with ethidium bromide. The size of the fragments of the normal and mutant allele is 75 and 99 bp respectively. Homozygote mutant: lane 1; homozygote wild type: lanes 2, 3, 4, 6 and 8; heterozygote: lanes 5 and 7. The additional larger fragment in case of heterozygotes is due to formation of a hybrid molecule consisting of a normal and mutant strand.

Figure 4:
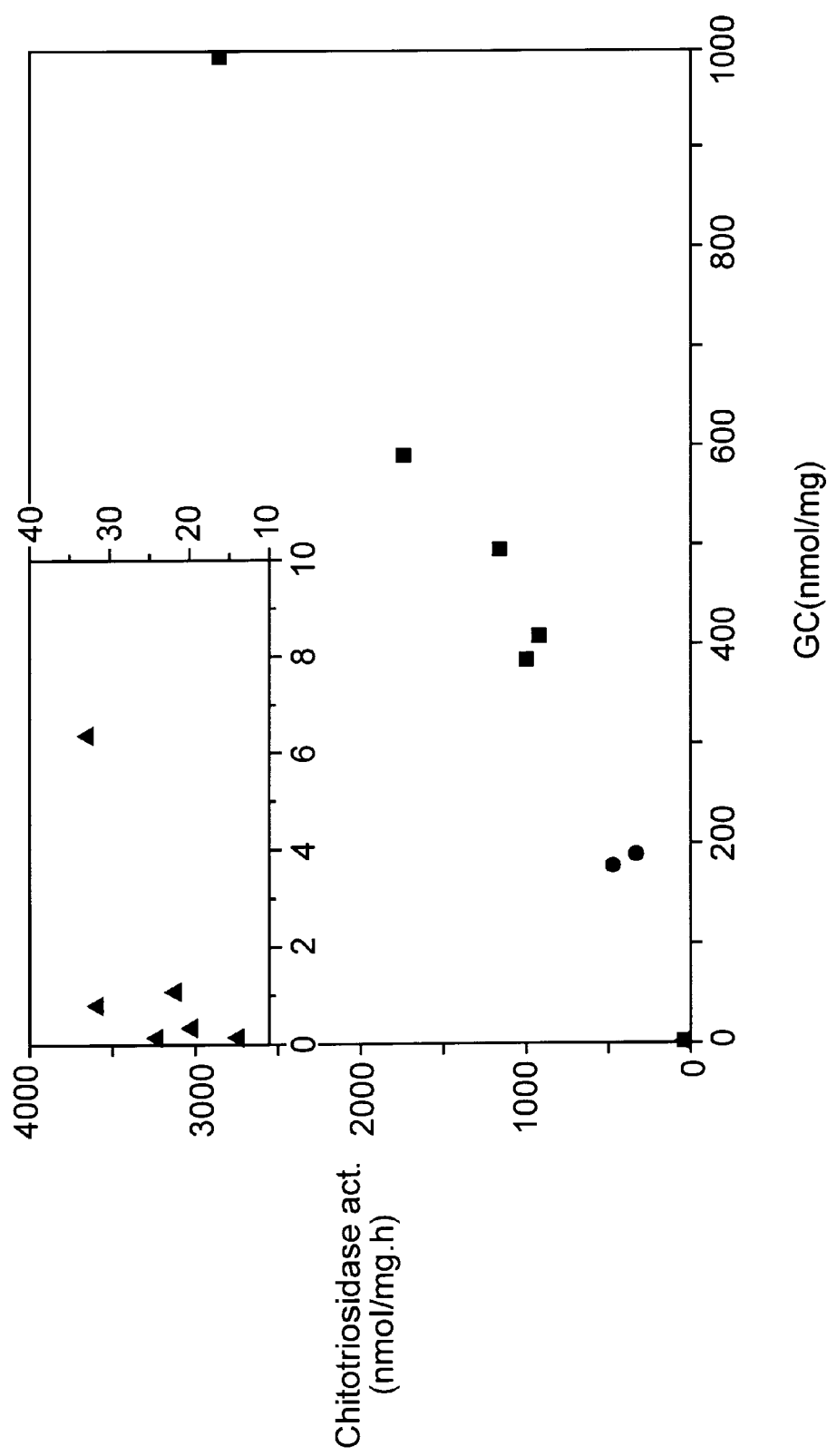

FIG. 4 shows the glucosylceramide and chitotriosidase levels in spleens from Gaucher Disease patients and normal subjects. Glucosylceramide levels (nmol/mg of wet weight tissue) and chitotriosidase levels (nmol/h/mg of wet weight tissue) were determined as described in Materials and Methods.

Figure 5:
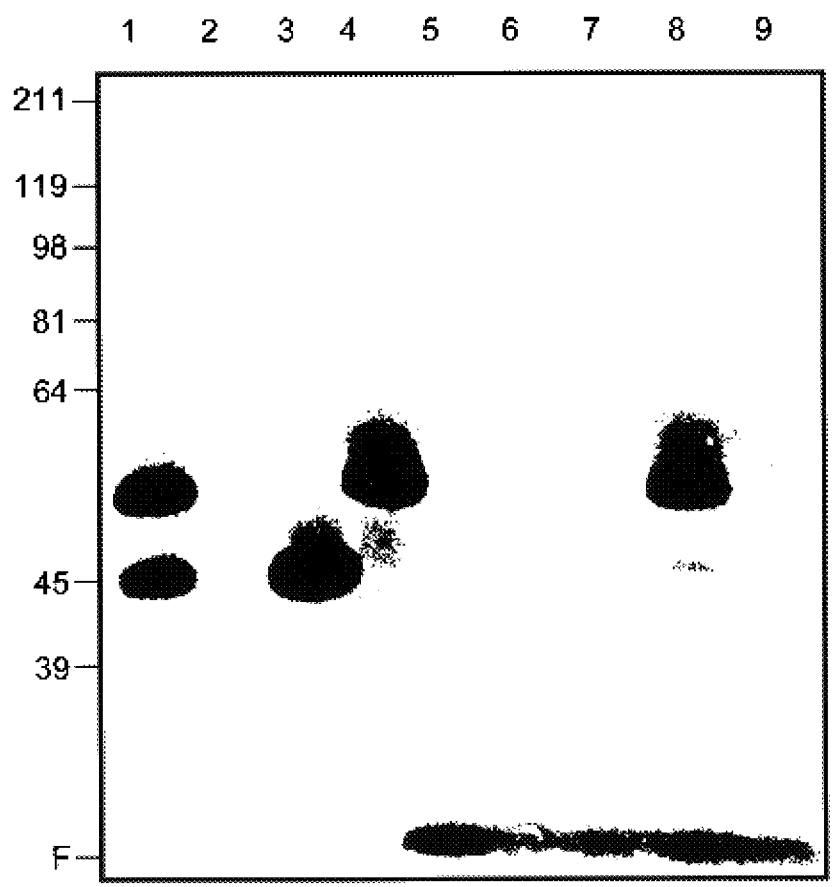

FIG. 5 shows an analysis of cell extracts on glycol chitin SDS-PAGE.

Protein samples were separated on 10% SDS-PAGE containing glycol chitin as described in Materials and Methods. Chitinase activity could be visualized as clearing zones in the gel. Lanes 1 and 2, 5 µg Gaucher spleen extract; lanes 3 and 4, medium of COS-1 cells transfected with the 39 kDa and 50 kDa chitotriosidase cDNA, respectively; lane 5, lysozyme; lanes 6 and 7, 10 µg neutrophil extract from a chitotriosidase-deficient person; lanes 8 and 9, 10 µg neutrophil extract of a control person. Samples in lanes 2, 7 and 9 were immuno-precipitated with an anti-(chitotriosidase) antiserum prior to electrophoretic separation. Molecular weight markers are indicated (kDa). The results shown are representative of several separate experiments. F=front of the gel.

Figure 6:
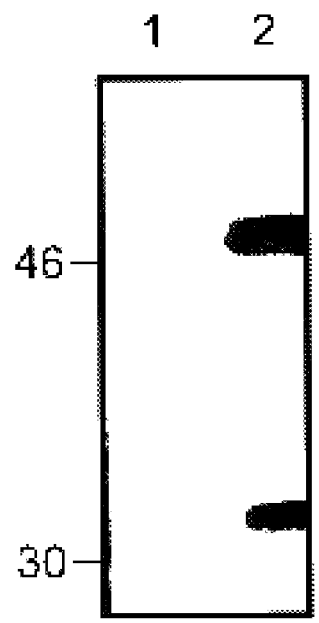

FIG. 6 shows metabolic labeling of lysosomal enzymes in neutrophils.

Neutrophils were metabolically labeled with radioactive methionine as described in Materials and Methods. Labeled cathepsin D was visualized after immunoprecipitation with specific antiserum (lane 2). No labeled chitotriosidase activity was detected after immunoprecipitation with an anti-(chitotriosidase) antiserum (lane 1). Molecular weight markers are indicated (kDa).

Figure 7A:
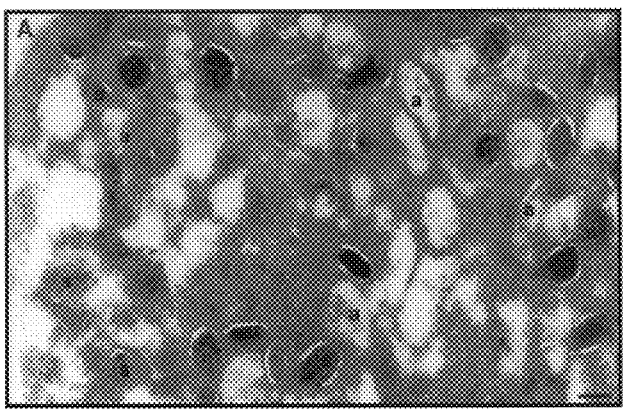
Figure 7B:
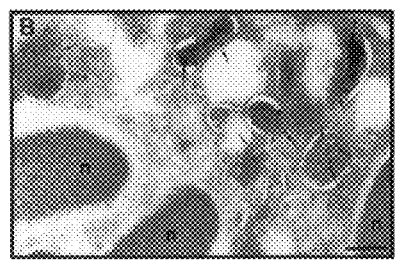
Figure 7C:
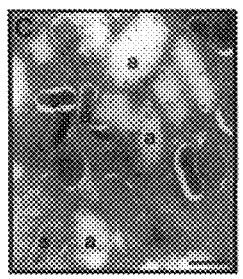

FIG. 7 are micrographs showing immuno double labeling of neutrophils for chitotriosidase and lactoferrin or myeloperoxidase.

Panels A and B, cryosections of neutrophils labeled to detect chitotriosidase (10 nm gold particles, large arrows in panel B) and lactoferrin (5 nm gold particles, small arrows in panel B). Chitotriosidase was found in association with the specific granules (s) which were marked with lactoferrin. The almost electron-lucent azurophilic granules (a) were not labeled. Background staining, e.g. over the nucleus (n) was negligible. Panel C, cryosection of a neutrophil labeled for chitotriosidase and MPO. The chitotriosidase (10 nm gold particles) was present in the electron-dense specific granules (s). The MPO (5 nm gold particles)-containing azurophil granules (a) did not contain chitotriosidase (10 nm gold particles). Bars, 200 nm.

Figure 8A:
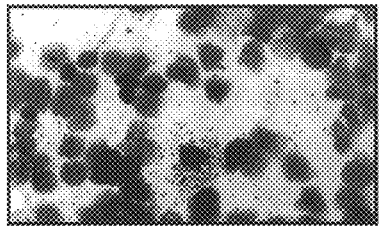
Figure 8B:
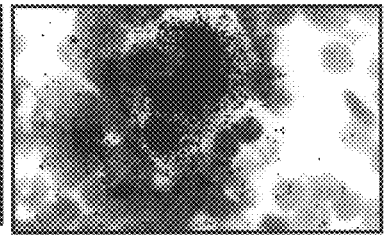
Figure 8C:
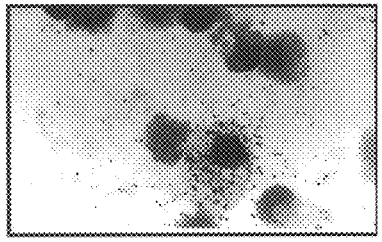

FIG. 8 is a visualization of chitotriosidase RNA in a bone marrow preparation from a type 1 Gaucher Disease patient.

Chitotriosidase mRNA expression in Gaucher bone marrow as visualized by in situ hybridization with a specific probe for chitotriosidase RNA. In the middle panel labeling of a multinucleated Gaucher cell is visible.

Figure 9:
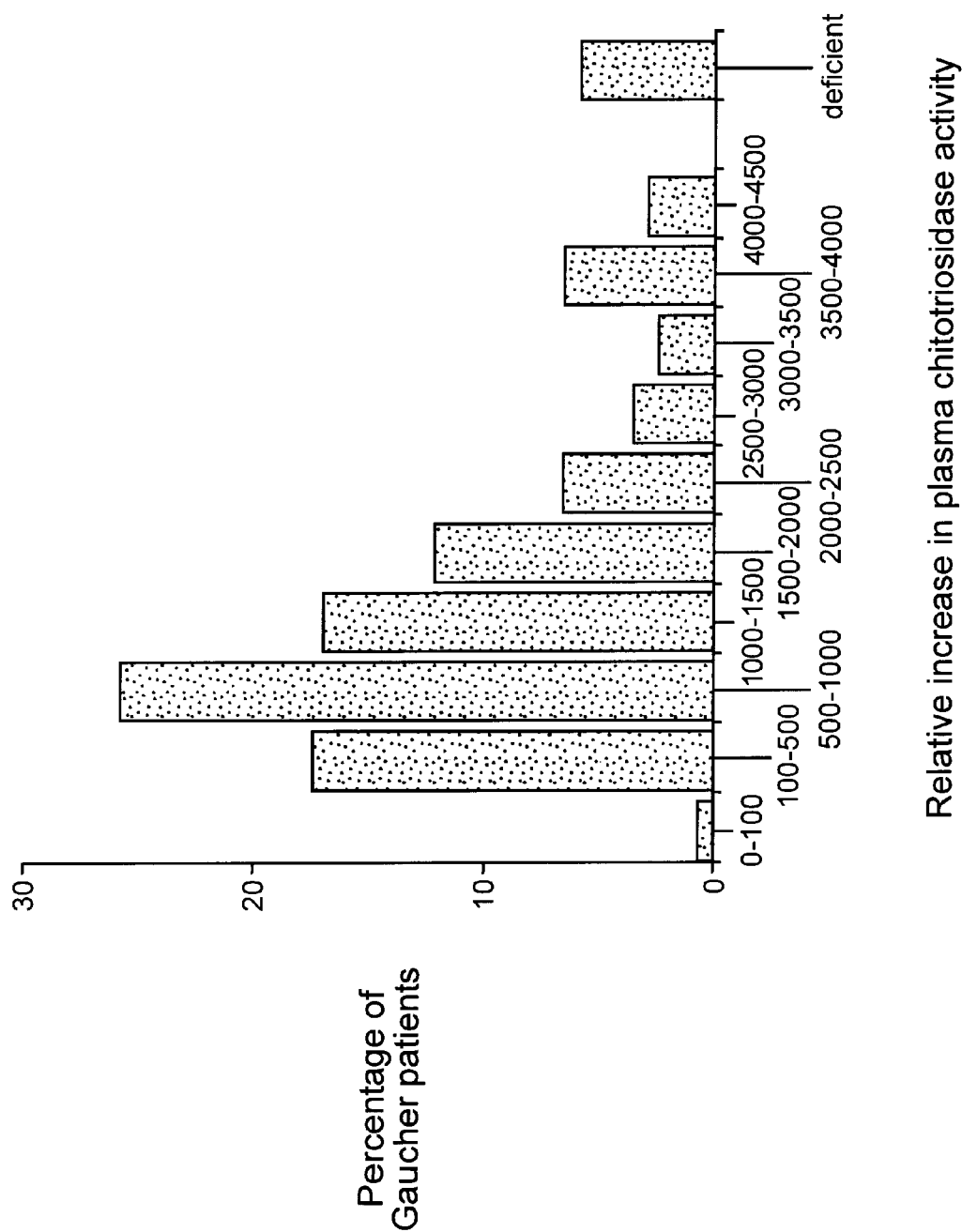

FIG. 9 is a distribution diagram showing the relative increase in plasma chitotriosidase activity among examined Gaucher Disease patients.

Patients are grouped based on the increase in their plasma chitotriosidase activity as related to the normal mean (23.4 nmol/ml. h). Chitotriosidase-deficient cases are also included in the distribution pattern.

Figure 10:
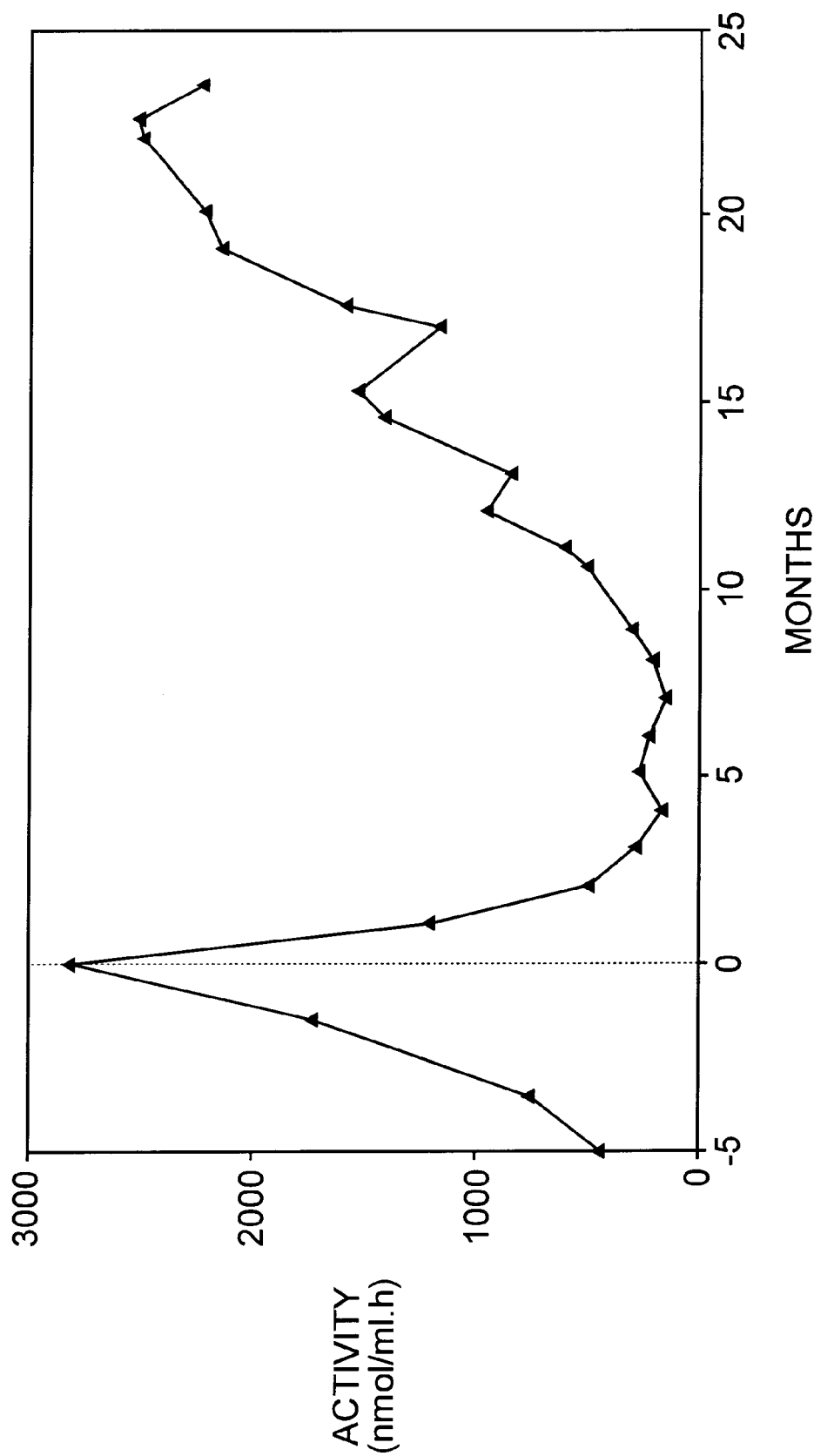

FIG. 10 shows the plasma chitotriosidase activity in a type 3 Gaucher Disease patient in relation to clinical manifestation of disease and therapy by chronic administration of glucocerebrosidase. Plasma enzyme level (x-axis, enzyme activity expressed in nmol/ml. h) rapidly increased after birth (t=5 months), preceeding onset of symptoms. Initiation of treatment (at t=0) was followed by marked correction in plasma chitotriosidase levels. The time (y-axis) is expressed in months.

Figure 11:
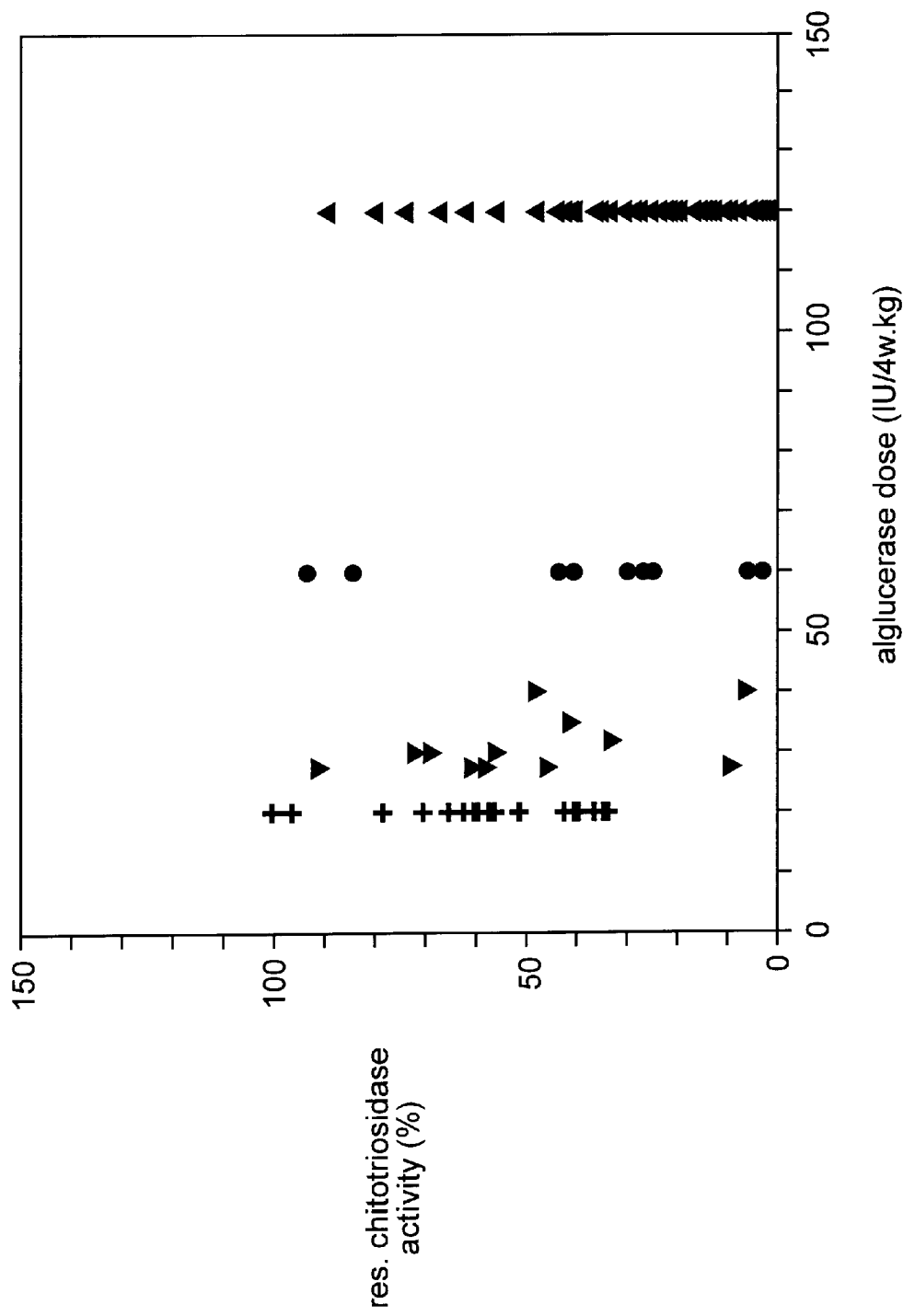

FIG. 11 shows the relationship between correction in plasma chitotriosidase level (expressed as percentage of initial plasma enzyme level) in Gaucher Disease patients that were treated with different doses of glucocerebrosidase (alglucerase) for a period of 10 months. Every symbol represents one patient. On the x-axis is shown the dose alglucerase (expressed in international units (IU) per kg body weight per 4 weeks) that each of the patients received.

Figure 12:
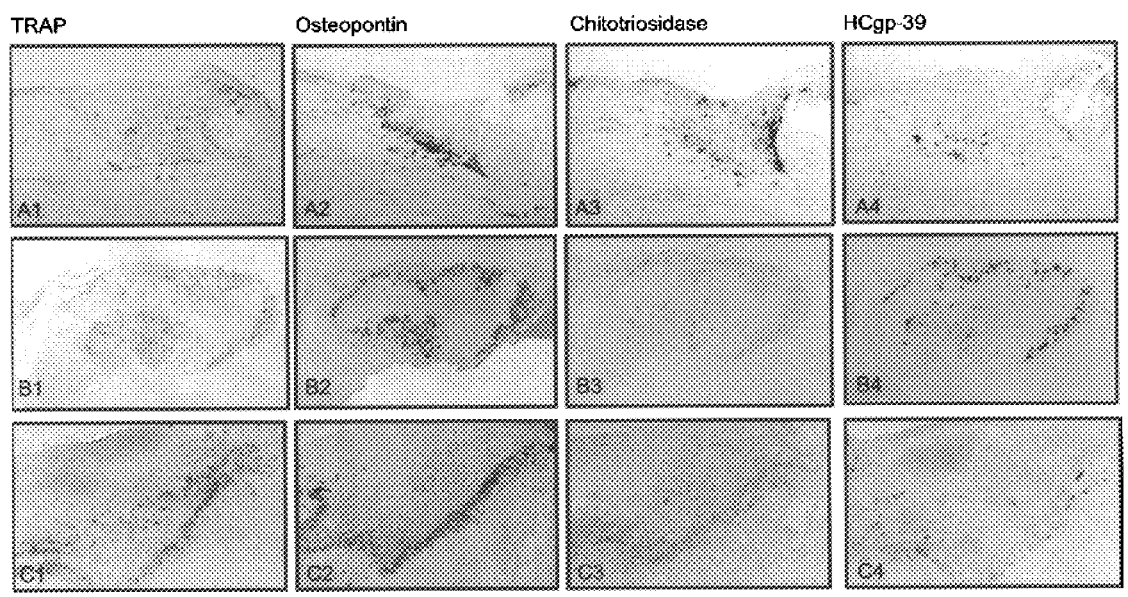

FIG. 12 shows in situ hybridization to localize mRNA encoding TRAP, osteopontin, chitotriosidase and HC gp-39 in human atherosclerotic plaques.

mRNA expression of these genes is disclosed upon in situ hybridization with [$^{35}$S]-radiolabeled anti-sense riboprobes in serial sections of atherosclerotic plaques. Hybridization of the probes was visualized with autoradiographic emulsion, resulting in black dots in the sections. Shown are: an aortic abdominal aneurysm (panel A), an early plaque of the iliac artery of an organ donor (panel B) and pathological material from a carotid artery (panel C). In A and C, the neointima of the vessel wall is shown, with the luminal side on the top and the media (not shown) at the bottom of the pictures. In B, sections of a separate neointimal region of an iliac artery are shown. Macrophages in the plaques were initially identified by immunohistochemistry with the antibody HAM56 (data not shown). In these specimen, all macrophages express TRAP, which is used in this experiment as a macrophage marker in the different plaques (A1, B1, C1). Osteopontin (A2, B2, C2), chitotriosidase (A3, B3, C3) and HC gp-39 (A4, B4, C4) are each expressed in partly different and partly overlapping subpopulations of macrophages. The arrow in A2 indicates expression of osteopontin in SMCs.

Figure 13:
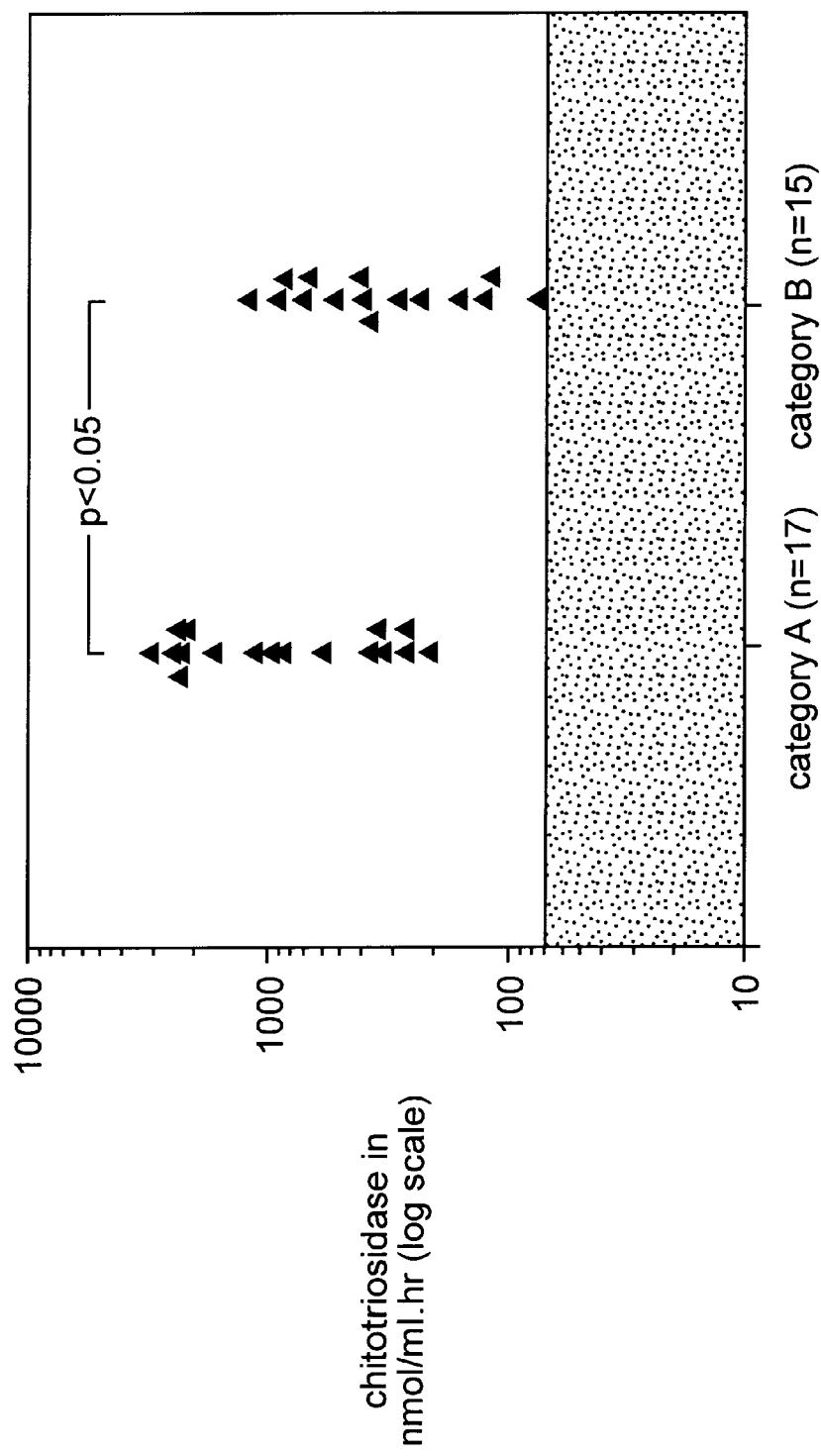

FIG. 13 shows chitotriosidase activity in patients with sarcoidosis divided in two categories: A=extensive disease, B=limited disease, dotted area=normal range.

Figure 14:
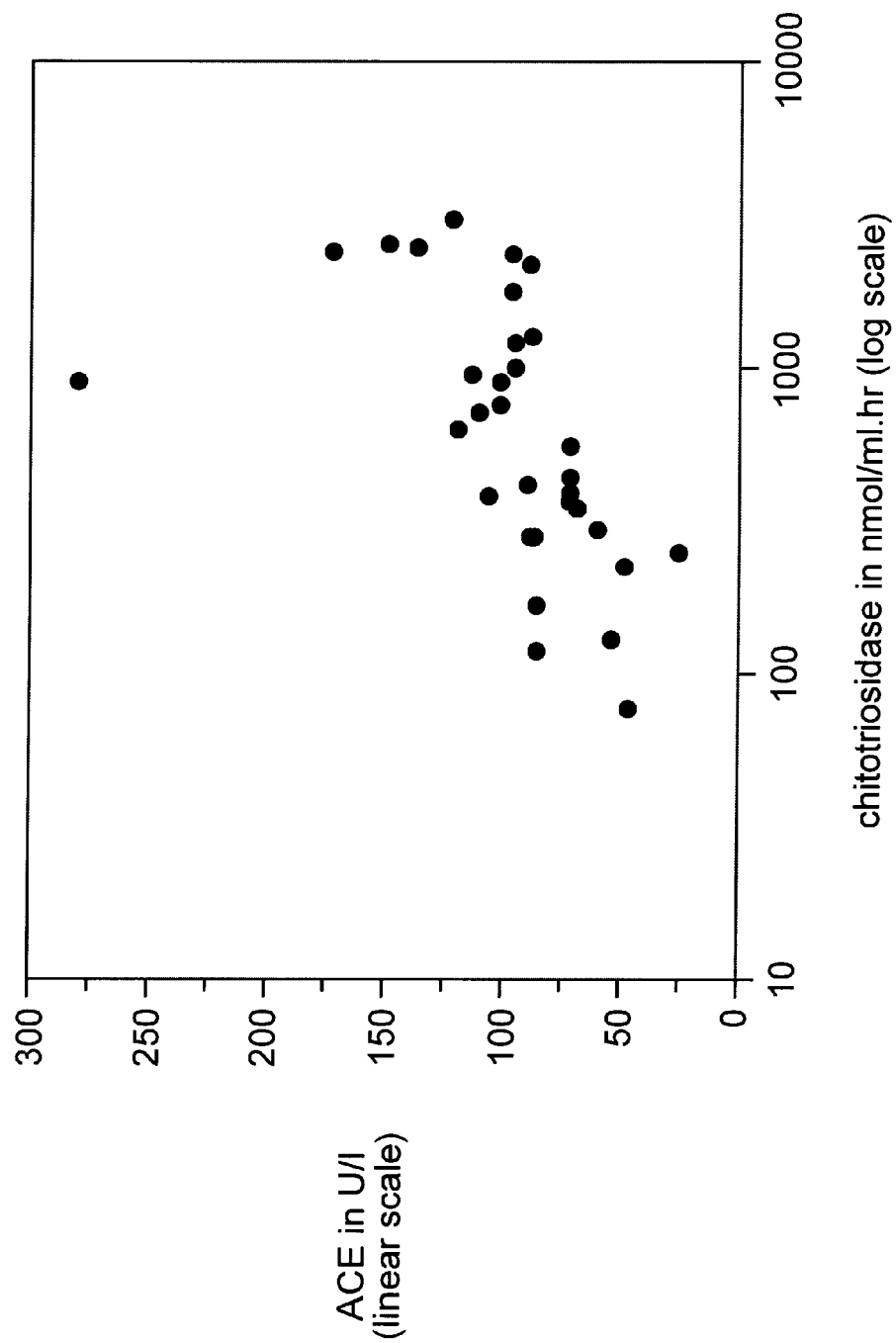

FIG. 14 shows a correlation between levels of chitotriosidase and ACE in patients with sarcoidosis (n=32, rho= 0.77, p<0.0005).

Figure 15:
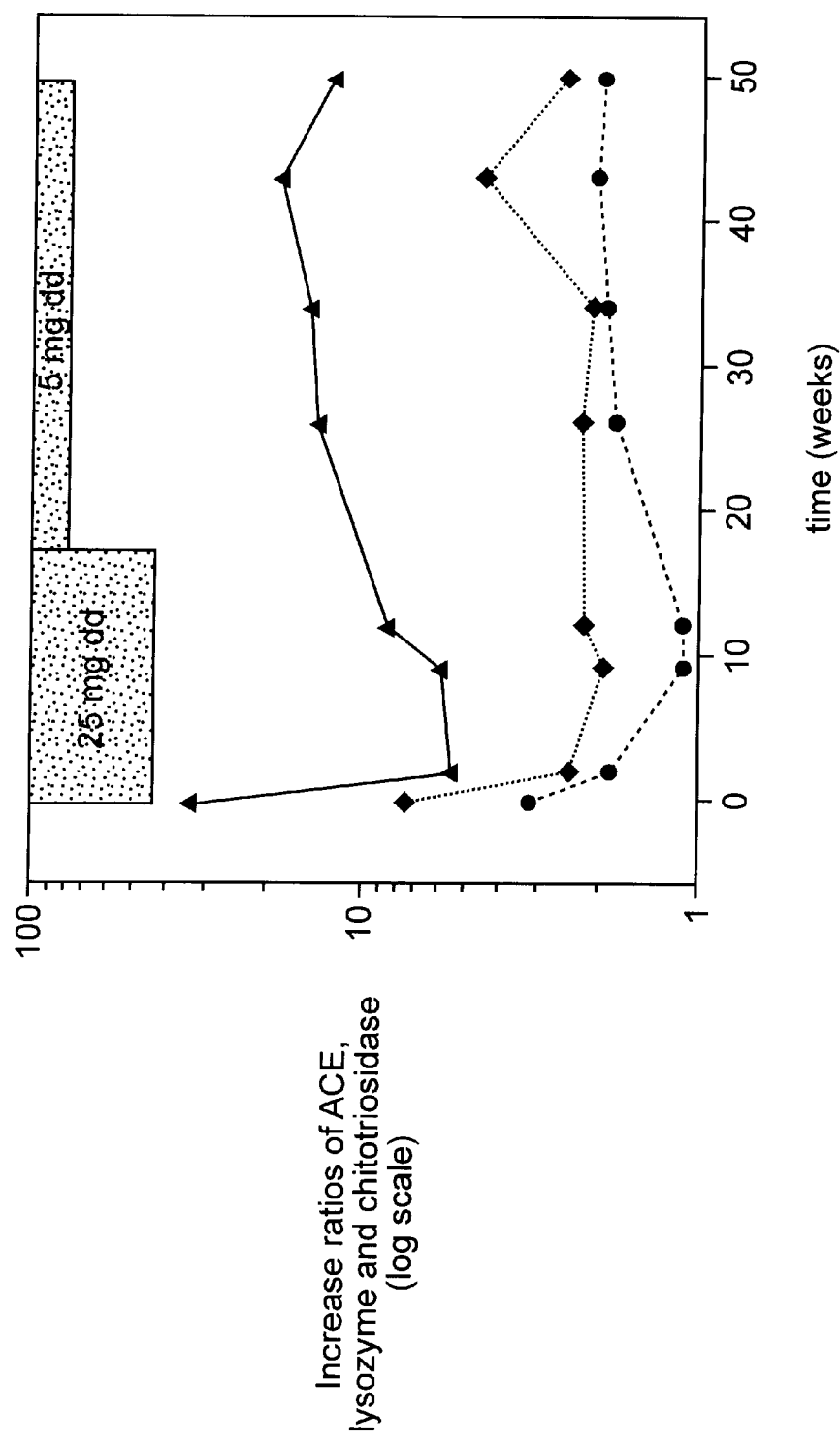

FIG. 15 shows the increase ratios of ACE (circles), lysozyme (diamonds) and chitotriosidase (triangles) during treatment with oral prednisone in patient 1 (dose per day in dotted area).

Figure 16:
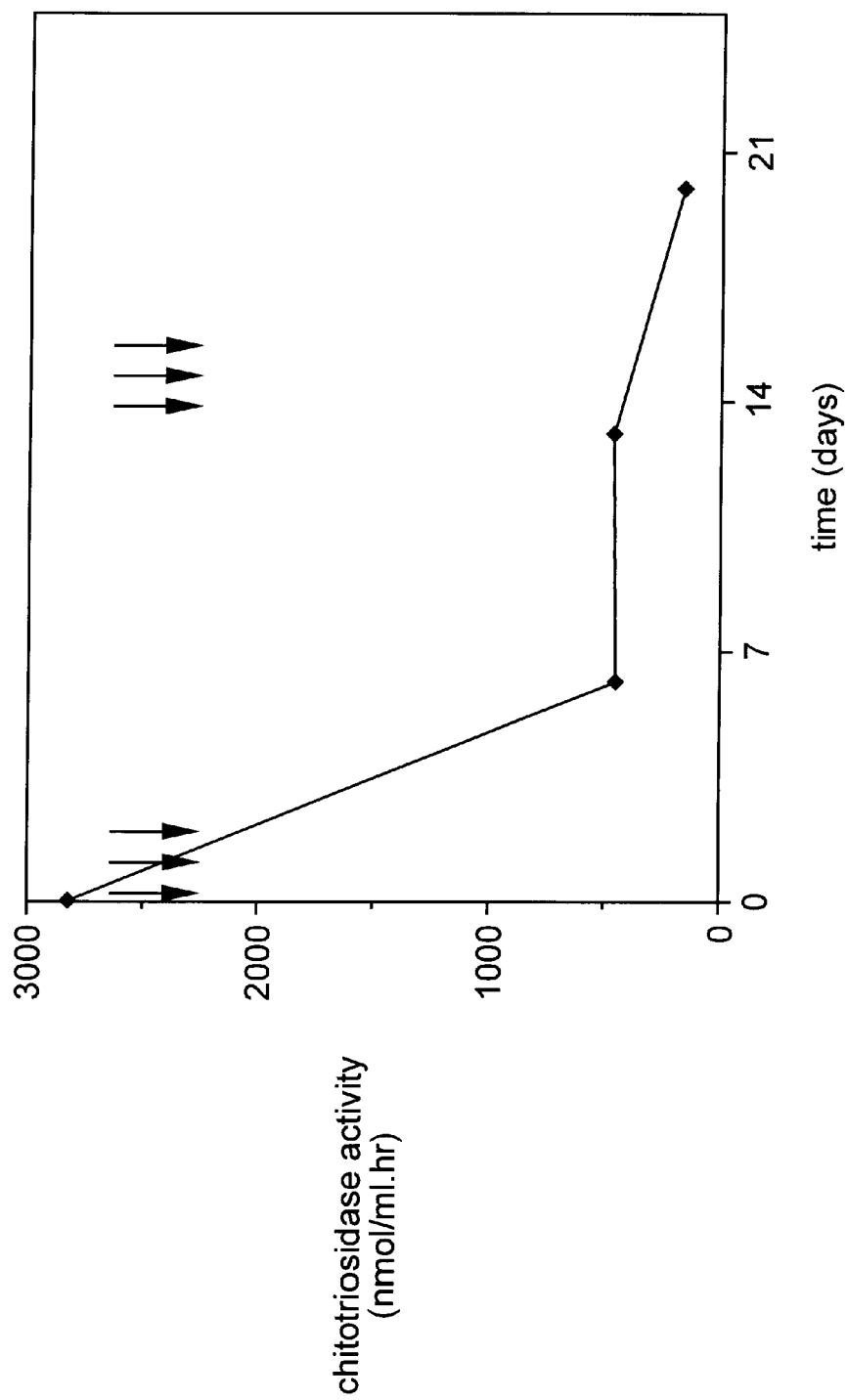

FIG. 16 shows the chitotriosidase activity during treatment with high dose intravenous methylprednisolone (arrow=500 mg) in patient 2.

Figure 17:
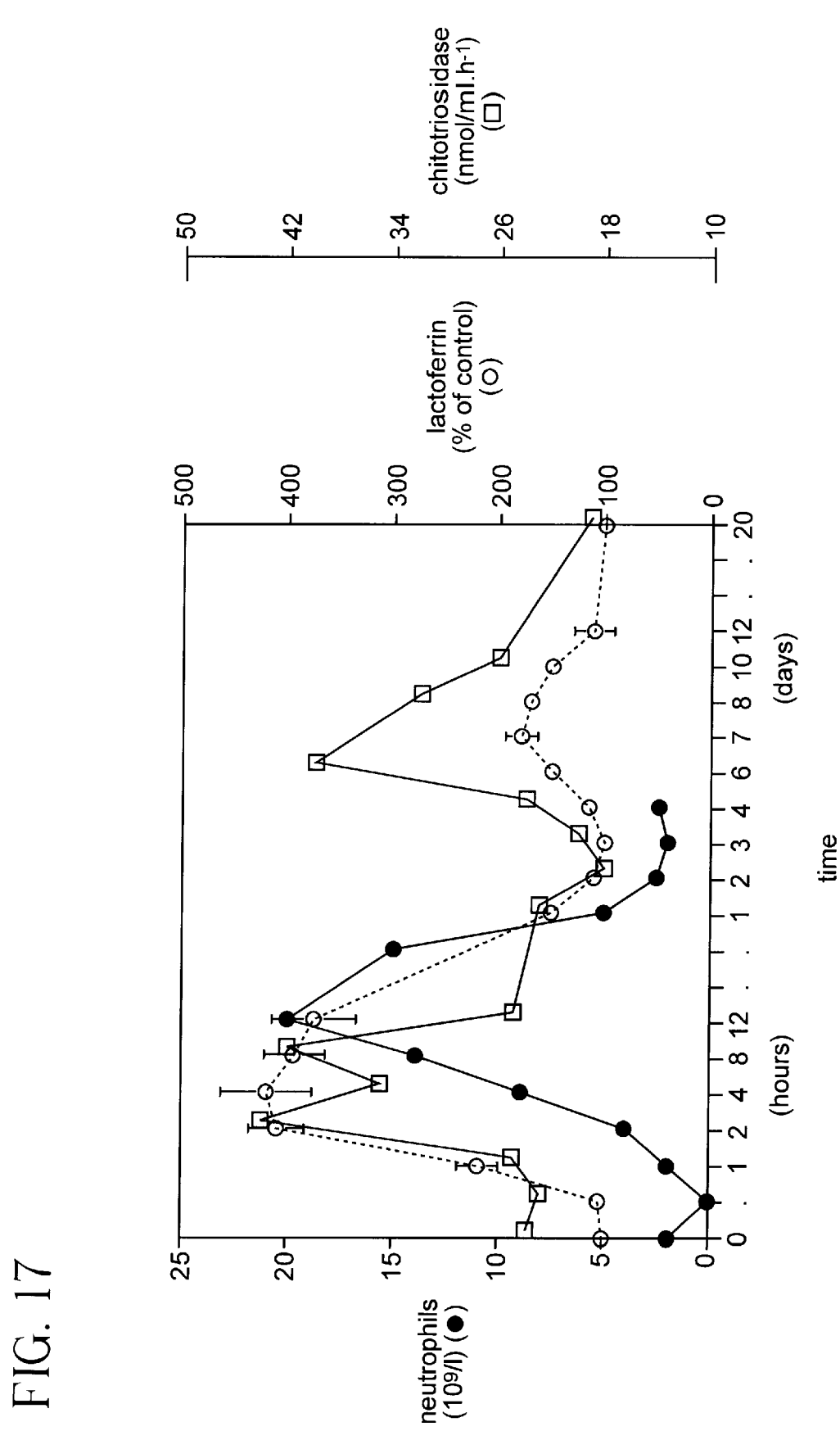

FIG. 17 shows the release of chitotriosidase and lactoferrin in the circulation after injection of G-CSF.

After injection of G-CSF, serum samples were analysed for neutrophils, lactoferrin, and chitotriosidase as described in Materials and Methods. Chitotriosidase activity (solid circles), lactoferrin concentration (open squares) and neutrophil count (open circles).

DETAILED DESCRIPTION

The present application describes that a defect in the chitotriosidase gene is a risk factor with respect to susceptibility for infectious diseases with chitin-containing pathogens and the development of (rheumatoid) arthritis.

Furthermore, the determination of the chitotriosidase genotype status of an individual described herein allows application of chitotriosidase as reliable diagnostic marker of activated macrophages in specific pathologies and improvements therein during therapy.

The molecular basis of the relatively common chitotriosidase deficiency has been determined by us, being a 24 bp duplication in the chitotriosidase gene. A convenient method has been developed allowing analysis of chitotriosidase genotype and subsequent determination of increased risk.

Chitotriosidase is shown to be a protein that is selectively secreted by macrophages upon specific activation and excreted by neutrophils by release of specific granules upon an appropriate stimulus. It has been conceived by us, and is here demonstrated, that the measurement of plasma chitotriosidase activity can be successfully used for diagnosis of specific disorders and monitoring of efficacy of therapeutic interventions, at least in combination with information on the chitotriosidase genotype status of an individual.

Therefore, in a first aspect the invention provides a process for determining the presence of a genetic disease risk factor in an individual comprising determining the chitotriosidase genotype of said individual.

This aspect of the invention can be applied to genomic DNA, RNA and RNA-derived cDNA.

In some embodiments, genomic DNA is examined to determine the presence of a wild type chitotriosidase gene, the presence of a mutant chitotriosidase gene, or both. The mutant chitotriosidase gene can be distinguished from the wild type chitotriosidase gene by the presence, in exon 10 of the gene, of a duplication of 24 nucleotides from the codons coding for amino acids Nos. 350 to 358 of chitotriosidase.

In other embodiments of the invention, RNA is examined to determine the presence of a wild type chitotriosidase RNA, the presence of a mutant chitotriosidase RNA, or both. Also, instead of RNA, cDNA derived from said RNA may be examined. In these embodiments, mutant chitotriosidase RNA (or cDNA) can be distinguished from wild type chitotriosidase RNA (or cDNA) by the absence of the 87 nucleotides coding for amino acids Nos. 344 to 372 of chitotriosidase.

In another aspect, the invention provides a process for determining the presence of activated phagocytes in a body fluid or tissue of an individual (most particularly a human person), under normal or pathological conditions, by subjecting a sample of said body fluid or tissue to an assay for determining the presence or amount therein of chitotriosidase protein, chitotriosidase enzyme activity, or chitotriosidase mRNA, in conjunction with a determination of the chitotriosidase genotype of said individual.

In a more specific aspect, the invention provides a process for diagnosing disease conditions which involve the presence of activated phagocytes, such as Gaucher disease, atherosclerosis, sarcoidosis, multiple sclerosis, arthritis, and Crohn disease, comprising determining the presence of activated phagocytes in a body fluid or tissue of an individual by subjecting a sample of said body fluid or tissue to an assay for determining the presence or amount therein of chitotriosidase protein, chitotriosidase enzyme activity, or chitotriosidase mRNA, in conjunction with a determination of the chitotriosidase genotype of said individual.

In another specific aspect, the invention provides a process for monitoring a therapeutic treatment of disease conditions which involve the presence of activated phagocytes, such as Gaucher disease, atherosclerosis, sarcoidosis, multiple sclerosis, arthritis, and Crohn disease, comprising determining the presence of activated phagocytes in a body fluid or tissue of an individual by subjecting a sample of said body fluid or tissue to an assay for determining the presence or amount therein of chitotriosidase protein, chitotriosidase enzyme activity, or chitotriosidase mRNA, in conjunction with a determination of the chitotriosidase genotype of said individual.

In a further aspect, the invention provides a test kit for determining the presence of a genetic disease risk factor in an individual by determining the chitotriosidase genotype of said individual, comprising means for isolating nucleic acid from said individual, means for amplifying a selected part of chitotriosidase-encoding nucleic acid, and means for analyzing amplified nucleic acid to distinguish wild type chitotriosidase nucleic acid from mutant chitotriosidase nucleic acid.

In some embodiments, said means for isolating nucleic acid is a means for isolating genomic DNA, said means for amplifying a selected part of chitotriosidase-encoding nucleic acid is a means for amplifying a selected part of chitotriosidase-encoding genomic DNA, and said means for analyzing amplified nucleic acid detects the presence of a duplication of 24 nucleotides from the codons coding for amino acids Nos. 350 to 358 of chitotriosidase to distinguish mutant chitotriosidase nucleic acid, which contains this duplication, from wild type chitotriosidase nucleic acid.

Preferably, said means for amplifying a selected part of chitotriosidase-encoding genomic DNA comprises PCR primers and optionally other PCR reagents, said PCR primers comprising a first primer which comprises a nucleotide sequence complementary to a first part of the chitotriosidase gene and a second primer which comprises a nucleotide sequence complementary to a second part of the chitotriosidase gene, wherein said first and second primers are complementary to opposite strands of the DNA and enclose the region coding for amino acids Nos. 350 to 358 of chitotriosidase.

In other embodiments, said means for isolating nucleic acid is a means for isolating mRNA, said means for amplifying a selected part of chitotriosidase-encoding nucleic acid is a means for amplifying a selected part of chitotriosidase-encoding mRNA or mRNA-derived cDNA, and said means for analyzing amplified nucleic acid detects the absence of the 87 nucleotides coding for amino acids Nos. 344 to 372 of chitotriosidase to distinguish mutant chitotriosidase nucleic acid, in which these nucleotides are missing, from wild type chitotriosidase nucleic acid.

Preferably, said means for amplifying a selected part of chitotriosidase-encoding mRNA or mRNA-derived cDNA comprises PCR, RT-PCR or NASBA primers and optionally other PCR, RT-PCR or NASBA reagents, said primers comprising a first primer which comprises a nucleotide sequence complementary to a first part of the chitotriosidase RNA and a second primer which comprises a nucleotide sequence complementary to the complement of a second part of the chitotriosidase RNA, and the primers enclose the region coding for amino acids Nos. 344 to 372 of chitotriosidase.

CHITOTRIOSIDASE GENE ABNORMALITY

We have noted that in plasma, leukocytes, tissues and urine samples of some subjects the chitotriosidase level is consistently extremely low [2]. In view of the fact that this trait was observed with increased incidence in some families, we decided to investigate the occurrence of a genetic basis.

ANALYSIS OF cDNA AND mRNA

Peripheral blood monocyte-derived macrophages from individuals with normal chitotriosidase activity and from individuals deficient in chitotriosidase activity were cultured [2]. From the cells RNA was isolated and single-stranded cDNA was prepared using reverse transcriptase and oligo (dT). From macrophage RNA chitotriosidase cDNA containing the complete open reading frame were generated using RT-PCR with the primers 5' CTG CAT CAT GGT GCG GTC 3' and 5' GAA GGC AAG GCT GAG AGC 3' [5]. [The abbreviation RT-PCR stands for a Polymerase Chain Reaction technology which also provides for Reverse Transcriptase activity, i.e. allows the formation of a complementary DNA strand from an RNA template. The Reverse Transcriptase activity may be provided by the presence of a separate reverse transcriptase enzyme, or by using a DNA polymerase having reverse transcriptase activity.]

Figure 1:
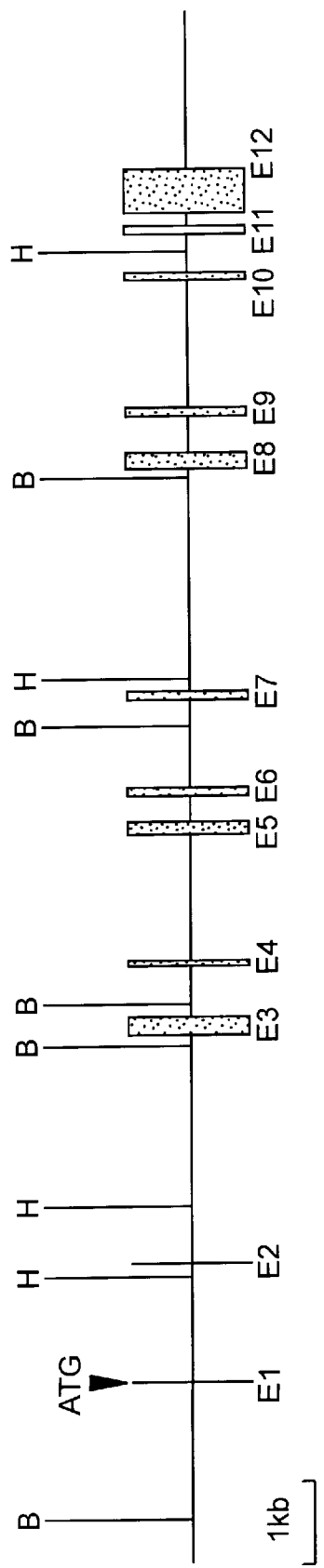
FIG. 1 shows the genomic organization of the chitotriosidase gene.

Sequencing showed that the chitotriosidase cDNAs from normal subjects and deficient individuals were completely identical to the previously reported sequence, with the exception of a deletion of 87 nucleotides in exon 10, see FIGS. 1 and 2. The abnormal mRNA codes for a protein that lacks amino acids 344–372, a highly conserved region in members of the chitinase protein family. Transfection of COS-1 cells with wild-type chitotriosidase cDNA resulted in secretion of enzymatically active 50 kDa chitotriosidase, whereas parallel transfection with mutant cDNA led to modest synthesis of a 47 kDa protein that was completely unable to degrade chitin or artificial substrates.

ANALYSIS OF GENOMIC DNA

To establish the precise molecular defect, genomic DNA of control subjects and chitotriosidase-deficient individuals was studied. Relevant parts of the mutant gene were amplified by PCR using appropriate primers. The following primers were employed: Chs8 5'-TAC ATC TTC CGG GAC AAC-3' and Chas9 5'-TCA GTT CCT GCC GTA GCG TC-3'. PCR fragments were cloned in the pGEM-T vector (Promega, Madison, Wis.) and sequenced as described in ref. 5.

Sequence analysis revealed that in exon 10 of the mutant gene a 24 bp duplication is present, see FIG. 3. This duplication leads to selection of a cryptic 3' splice site downstream in the exon. Although the authentic splice site is still intact in the mutant chitotriosidase gene, it appears to be no longer selected in the presence of the duplication.

CONVENIENT DETECTION OF CHITOTRIOSIDASE GENE ABNORMALITY

The presence of the 24 bp duplication in the chitotriosidase gene can be detected, for example by PCR of genomic DNA with specific primers. For example, the following primers can be used: Chs9 (5'-AGC TAT CTG AAG CAG AAG-3') and Chas8 (5'-GGA GAA GCC GGC AAA GTC-3'). The following PCR conditions can be used: 150 ng of each primer, 1.5 U Taq polymerase (Promega) and appropriate PCR buffer: inital denaturation for 5 min at 95 C., followed by 25 cycles of 30 sec 95° C., 30 sec 55° C., 30 sec 74° C., and a final extension for 5 min at 74° C. [Other conditions can be used as well, however.]

With this PCR procedure fragments of 75 bp and 99 bp from the normal and mutant gene are amplified, respectively.

As shown in FIG. 3, individuals with a homozygous wildtype chitotriosidase genotype, individuals with homozygous mutant chitotriosidase genotype and individuals with heterozygous chitotriosidase genotype can be nicely identified. In the case of heterozygotes an additional larger fragment is formed by the PCR reaction (see FIG. 3). This is due to formation of a hybrid DNA molecule, consisting of a normal strand that is annealed with a mutant strand.

ALTERNATIVE PROCEDURES FOR DETERMINATION OF CHITOTRIOSIDASE GENOTYPE

Based on the established nucleotide sequence of the normal and mutant chitotriosidase gene, a variety of alternative procedures may be used that will also allow determination of chitotriosidase genotype status of an individual. A number of examples in this connection are presented herein, but these are not intended to limit the invention.

Firstly, alternative primers to the ones described above may be employed for amplification of genomic DNA. The primers might differ in length and position, provided their use results in generation of differently sized PCR fragments when genomic mutant and control DNA are used as template. Some examples:
- (i), shorter (or longer) primers:
  5'-TAT CTG AAG CAG AAG-3' and 5'-GAA GCC GGC AAA GTC-3': generating fragments of 69 bp (wt) and 93 bp (mut)
- (ii), primers shifted along the template:
  5'-CTC CCT GCA CAG GTC AGC-3' and 5'-GTA TCG GCC CTG GTT GCA-3': generating fragments of 108 bp (wt) and 132 bp (mut).

Alternatively, cDNA instead of genomic DNA may be used for mutation analysis. As already described above, mutant chitotriosidase cDNA contains a 87 nucleotide deletion as compared to the wildtype chitotriosidase cDNA. Again, a variety of primer sets may be used to obtain differently sized fragments from mutant and wildtype cDNA that can be detected by fragment size analysis.

Instead of separation of amplified control and wildtype chitotriosidase fragments by gel electrophoresis, direct sequencing of the fragments (derived from cDNA or genomic DNA) may be used.

For the demonstration of the presence of wildtype and/or mutant cDNA use may be made of RNase protection analysis. This method is based on the principle that RNA is hybridized with a specific labelled RNA probe. The RNA is only protected against digestion with a single-strand ribonuclease when it has hybridized. RNA probes can be obtained by cloning the target RNA fragment in a transcription vector under the control of a bacteriophage promoter. Using the appropriate RNA polymerase a labelled complementary RNA probe can be generated. In the case of chitotriosidase the following RNase protection probe can be used:

5'TAC ATC TTC CGG GAC AAC CAG TGG GTC GGC TTT GAT GAT GTC GAG AGC TTC AAA ACC AAG GTC AGC TAT CTG AAG CAG AAG GGA CTG GGC GGG GCC ATG GTC TGG GCA CTG GAC TTA GAT GAC TTT GCC GGC TTC TCC TGC AAC CAG 3'. Protected fragments of 140 nt (wt) and 60 nt (mut) will be generated with this probe.

As an alternative method use may be made of the difference in nucleotide sequence between mutant and wildtype genomic DNA. For example the mutant genomic chitotriosidase DNA contains a unique sequence that can be cleaved by the restriction enzyme BfaI and is absent in the wildtype genomic chitotriosidase DNA. Another possibility is to make use of mismatch primers that generate a unique restriction site in wildtype or mutant genomic DNA or cDNA. For example, the use of a set of mismatch primer 5' GGC GGG GCC ATG GCC T 3' and normal primer 5' GGA GAA GCC GGC AAA GTC 3' will generate PCR fragments of 51 bp (wt) and 51 bp and 75 bp (mut). After digestion with restriction enzyme AvrII the 75 bp is cleaved into a 59 and 16 bp fragment.

Alternative 'state of the art' strategies for mutation detection can be employed as well. For example, SSCP (single strand conformation polymorphism) and DGGE (denaturing gradient gel electrophoresis) for the detection of the presence of an abnormality in appropriate fragments of chitotriosidase cDNA (87 nucleotide deletion) or genomic DNA (24 bp duplication) can be used.

Another possibility is to make use of differences between genomic mutant and wildtype chitotriosidase DNA with respect to their hybridization with specific probes. Again, on the basis of the known differences in nucleotide sequences of mutant and wildtype genomic chitotriosidase DNA a variety of suitable probes may be composed. Sequence-specific monitoring of PCR products is routinely performed by hybridization analysis using blots, gels or microtiter plates. The hybridization of small oligonucleotide probes to template DNA can be visualized with radioactively or fluorescently labeled probes, or chemiluminescence techniques.

Another possibility is to use the ligase chain reaction (LCR). With this method a thermostable DNA ligase is used to detect single base changes or duplications/deletions in genes of interest. The enzyme specifically links two adjacent oligonucleotides when hybridized to a complementary target only when the oligonucleotides are perfectly base paired at the junction. Ligated oligonucleotide products are amplified by thermal cycling of the ligation reaction. The duplication in the chitotriosidase gene will allow detection of the mutated allele by LCR.

Also other nucleic acid amplification techniques may be used. Especially in the case that the genotype analysis is applied to RNA, use of NASBA technology or RT-PCR technology are preferred.

OCCURRENCE OF THE MUTATION

All chitotriosidase-deficient individuals examined so far (n=25) are homozygous for the 24 bp duplication in the chitotriosidase gene.

The frequency of the mutant chitotriosidase allele (containing the 24 bp duplication) was determined for unrelated individuals living in The Netherlands, Indonesia and for Ashkenazim. The incidence of homozygotes and heterozygotes for the duplication was 6% and 36%, respectively for the Dutch indivuals (n=100); 8% and 36% for the Indonesian individuals (n=80); and 7% and 37% for the Jewish individuals (n=80).

The 24 bp duplication in the chitotriosidase gene was detected in individuals with various ethnic background, such as individuals from South Africa and West Africa, various European countries, and Japan. The findings suggest that the duplication must have an ancient origin.

Based on the incidence of chitotriosidase deficiency in The Netherlands of about 6%, the Hardy-Weinberg equilibrium predicts that 37% of the population will be carrier of a mutant chitotriosidase gene. This prediction corresponds well with the observed frequency of carriers of the 24 bp duplication in the chitotriosidase gene. This and the finding that all chitotriosidase-deficient individuals so far are homozygous for the duplication, indicates that this mutation must be the predominant cause of chitotriosidase deficiency.

APPLICATIONS

1. Determination of Chitotriosidase Genotype to Assess Susceptibility for Infection with Chitin-Containing Pathogens In particular when the immune system is suppressed, the resistance against infections relies heavily on innate defense mechanisms. Chitotriosidase is an important component of the innate immune system. Individuals deficient in chitotriosidase have an increased chance on reduced resistance against infections with chitin-containing pathogen.

Chitotriosidase genotype analysis will be useful with respect to decision making on prophylactic treatment against infections of individuals with a suppressed immune system. In the case of homozygosity or heterozygosity for the 24 bp duplication in the chitotriosidase gene prophylaxis should be considered.

The chitotriosidase genotype can be determined by demonstration of the 24 bp duplication in the chitotriosidase gene, for example with the described PCR methodology.

2. Determination of Chitotriosidase Genotype to Assess Risk for (Rheumatoid) Arthritis Chitotriosidase is highly homologous to human cartilage glycoprotein of 39 kDa (Hcgp39) [6]. We have demonstrated that Hcgp 39 can be viewed as the lectin counterpart of chitotriosidase [7]. Hcgp39 is produced by chondrocytes and macrophages [5,8] and is thought to play a role as a pathological autoantigen in (rheumatoid) arthritis [9]. Hcgp 39 levels are elevated in synovial fluid of patients with rheumatoid arthritis [8].

In contrast to chitotriosidase, Hcgp39 does not hydrolyze chitin but instead binds firmly to the poly-N-acetylglucosamine (i.e. chitin) due to the substitution of critical aminoacid in the catalytic center region. Hcgp 39 and chitotriosidase will have the same ligand and substrate, respectively. In other words, the presence of chitotriosidase will effect the presence of the ligand for Hcgp39. Binding of Hcgp39 to its ligand will influence the immunological properties of the protein. The chitotriosidase genotype of an individual will therefore effect the risk that Hcgp39 acts as autoantigen and induces (rheumatoid) arthritis.

The chitotriosidase genotype of an individual can be determined by demonstration of the 24 bp duplication in the chitotriosidase gene.

3. Determination of Chitotriosidase Genotype for Interpretation of Chitotriosidase Activity Measurements Chitotriosidase is elevated in some disease conditions and has a diagnostic value as such (see below). Moreover, monitoring of changes in enzyme activity are useful to follow efficacy of therapeutic intervention. A nice example of this is formed by Gaucher disease, a macrophage disorder in which chitotriosidase is on average 1000-fold elevated in the blood. Upon successful therapeutic intervention the enzyme activity levels are corrected, whereas unsuccessful treatment is reflected in no or a poor correction in plasma chitotriosidase activity.

Individuals that are homozygous for the chitotriosidase defect show no true chitotriosidase activity. However, the presence of some distinct enzyme in plasma may cause the presence of some residual activity against chitotrioside substrate. The exact status of the individual, being homozygous or heterozygous for the defect in the chitotriosidase gene, can be determined by analysis of the chitotriosidase genotype as described above. Carriers for the chitotriosidase defect show on average half the chitotriosidase levels observed for individuals with a wildtype chitotriosidase genotype. For example, the mean plasma chitotriosidase activity was 35.6 nmol/ml. hour in the case of 50 normal subjects with a wildtype chitotriosidase genotype and 19.7 nmol/ml. hour in the case of 50 age- and sex-matched normal subjects that were carrier for the chitotriosidase mutation. The mean plasma chitotriosidase activity was 17.540 nmol/ml. hour in the case of 30 type 1 Gaucher patients with a wildtype chitotriosidase genotype and 9.034 nmol/ml. hr in the case of 30 clinically comparable patients that were carrier for the chitotriosidase mutation. These findings illustrate clearly that in order to interpret the values on chitotriosidase activity level in an individual the chitotriosidase genotype has to be taken into account and thus needs to be determined. This determination may be performed by detection of the presence of the 24 bp duplication in the chitotriosidase gene.

CLINICAL VALUE OF CHITOTRIOSIDASE ACTIVITY MEASUREMENT AND RELATED CHITOTRIOSIDASE GENOTYPING

Activated Phagocytes: The Source of Chitotriosidase

After the discovery of the marked elevation in plasma chitotriosidase it was investigated by us what the precise origin of the excessive plasma enzyme is. Our studies revealed that the pathological lipid-laden macrophages themselves synthesize and secrete massively chitotriosidase into the circulation. Firstly, in samples of spleens of symptomatic Gaucher patients the levels of glucosylceramide, which are a direct measure of the amount of Gaucher cells, correlate with chitotriosidase activity levels (see FIG. 4). Secondly, in situ hybridization with a specific chitotriosidase RNA probe showed massive labeling of Gaucher cells in liver, spleen, marrow and lung. The excessive chitotriosidase in plasma of Gaucher patients therefore originates from the pathological Gaucher cells in various tissues.

Gaucher cells are glucosylceramide-laden macrophages. Macrophages, like neutrophils, are phagocytes. The phagocytes are the most important group of long-lived phagocytic cells. The phagocytes are all derived from bone marrow stem cells, and their function is to engulf particles, including infectious agents, internalize them and destroy them. We have investigated to which extent chitotriosidase is a general marker for activated phagocytes.

Neutrophils

We studied in detail blood cells with respect to the production of chitotriosidase. It had been demonstrated by us [2] that peripheral blood leukocytes contain chitotriosidase. Table 1 shows the chitotriosidase activity levels in plasma and corresponding leukocytes from control subjects and Gaucher patients. The phenomenon of chitotriosidase deficiency can be also seen.

Upon separation of leukocytes into different cell types by counterflow elutriation no chitotriosidase activity was detectable in lymphocytes or monocytes from human peripheral blood. At least 95% of the enzyme activity in leukocytes can be ascribed to neutrophilic granulocytes. Table 2 shows the chitotriosidase activities in neutrophils.

In tissues two major distinct forms of chitotriosidase occur: an O-glycosylated 50 kDa protein with heterogenous isoelectric point and a non-glycosylated 39 kDa protein with isoelectric point of 8.1 [6,10]. In neutrophils almost exclusively the 50 kDa protein is present. This can be visualized by Western blotting, but also for instance by analysis with 'glycol chitin SDS-PAGE' [11]. With the latter method protein samples are separated at non-reducing conditions on 10% SDS polyacrylamide gels containing glycol chitin. After electrophoresis, chitotriosidase in the gel is renatured by excessive washing in casein buffer for 8 hours chitotriosidase. The renatured enzyme degrades the glycol chitin in the gel. The enzyme activity can be visualized as clearing zones in the gel upon staining of glycol chitin with Calcofluor. FIG. 5 shows that the chitotriosidase in neutrophils behaves identical to pure 50 kDa chitotriosidase with glycol chitin SDS-PAGE.

Next the synthesis of chitotriosidase in neutrophils was studied by metabolic labeling with radioactive methionine and analysis of subsequent formation of labelled chitotriosidase and cathepsin D, exactly as described earlier for macrophages [10]. FIG. 6 shows that the synthesis and processing of the lysosomal hydrolase cathepsin D in neutrophils can be visualized in this manner. Despite the fact that the anti-chitotriosidase antiserum precipitated all chitotriosidase activity in neutrophils, no labelled chitotriosidase was detected in the metabolic labeling experiments. Using high quantities of total neutrophil RNA, PCR-amplification with various chitotriosidase specific primers was negative. This suggests that the mature neutrophils in peripheral blood are not synthesising chitotriosidase due to absence of its mRNA.

We demonstrated earlier that in macrophages chitotriosidase is present in lysosomes [10]. To determine its subcellular localization in neutrophils cells were treated with different combinations of stimuli to obtain differential degranulation of intracellular granules [12]. Table 3 shows that exposure of pure neutrophils to a condition which induces secretion of secretory vesicles (incubation with platelet activating factor (PAF)) does not result in the release of chitotriosidase. Exposure of neutrophils to PAF+N-formyl-methionyl-leucyl-phenylalanine (fMLP), which also induces the release of specific granules, results in almost complete secretion of chitotriosidase activity. Finally, exposure to cytochalasin B+fMLP, which causes the secretion of proteins from all vesicles including azurophilic granules, does not result in further substantial secretion. This is in contrast to the behaviour of the lysosomal enzyme beta-hexosaminidase. These results indicate that in neutrophils chitotriosidase is not present in the lysosome-like azurophilic granules, but in the specific granules. To verify this, immunogold double-labeling experiments on cryosections of resting neutrophils were performed. The two predominant types of granules, specific and azurophilic, were identified with antibodies against lactoferrin and myeloperoxidase (MPO), respectively. FIG. 7 shows that no labeling for chitotriosidase is detectable in MPO-containing azurophilic granules and that labeling for chitotriosidase occurs of lactoferrin-containing specific granules.

The localisation of chitotriosidase in specific granules explains the absence of mRNA in mature neutrophils. It is known that constituents of specific granules, for example lactoferrin, are synthesized only during a specific stage in the maturation of precursors of neutrophils in the bone marrow, the meta-myelocyte stage [13].

Macrophages

As we described earlier [5,10], peripheral blood monocytes that are cultured for prolonged time and concomittantly mature into activated macrophages are also capable to synthesize chitotriosidase. Chitotriosidase is only expressed after several days of culture when the cells have developed into activated macrophages (see also U.S. patent application Ser. No. 08/486,839).

In macrophages initially an O-glycosylated 50 kDa chitotriosidase protein is produced that is largely secreted. Part of the 50 kDa protein is C-terminally processed into a non-glycosylated 39 kDa protein that accumulates in lysosome [10]. We were able to detect small quantities of chitotriosidase enzyme and mRNA in alveolar macrophages and synovial A cells, but not in Kupffer cells and peritoneal macrophages. This suggests that macrophages have to be specifically activated in order to express chitotriosidase.

THE APPLICATION OF CHITOTRIOSIDASE TO MONITOR ACTIVATED PHAGOCYTES IN RELATION TO DIAGNOSIS AND THERAPY

The demonstration that chitotriosidase is specifically released by phagocytes (i.e., stimulated neutrophils and specifically activated macrophages) led us to hypothesize that the enzyme may be a useful marker to monitor the presence of such specifically activated phagocytes in relation to diagnosis and monitoring of therapy of disease conditions.

EXAMPLE 1

Gaucher Disease

1. Detection of Pathological Macrophages (Gaucher Cells)

As described above, Gaucher cells express high quantities of chitotriosidase mRNA (see FIG. 8 for an example) and tissues containing the storage cells show high chitotriosidase activity levels (see above). Provided that an individual is not deficient in chitotriosidase, the presence of Gaucher cells can be monitored by detection of chitotriosidase protein or mRNA. Since chitotriosidase is largely a secretory protein high levels of the enzyme (activity) can be demonstrated in plasma and urine samples.

2. Diagnosis

Confirmation of Symptomatic Gaucher Disease

In all symptomatic Gaucher patients, provided that they are not genetically deficient in chitotriosidase, plasma enzyme activities are dramatically activated, being at least 100-fold the corresponding normal value. FIG. 9 gives an overview of the extent of plasma chitotriosidase elevation in symptomatic Gaucher patients (n=500). It can be seen that the vast majority of patients shows plasma enzyme levels that are several hundred fold elevated. The detection of such dramatic elevation in chitotriosidase can be employed for confirmation of diagnosis of Gaucher disease.

Early Detection of Onset of Gaucher Disease

Due to the poor predictive value of glucocerebrosidase genotype with respect to manifestation of Gaucher disease and due to the highly heterogeneous clinical symptoms of the disorders, the early detection of the accumulation of storage cells in Gaucher patients is of great clinic importance. Monitoring of plasma chitotriosidase activity is extremely useful in this connection. This is for example illustrated by the following example. In a family with previous incidence of type 3 Gaucher disease (L444P glucocerebrosidase homozygote), a second child with the same mutant genotype was born. Plasma chitotriosidase activity levels were monitored from birth. FIG. 10 shows that enzyme levels rapidly increased, prior to the manifestation of clinical signs. The rapid accumulation of storage cells, as illustrated by plasma chitotriosidase increment, led to the decision to initiate treatment (see below).

3. Monitoring of Efficacy of Therapeutic Intervention

Therapeutic intervention of Gaucher disease is based on the concept to remove and/or prevent formation of Gaucher cells. Successful therapy of symptomatic Gaucher patients therefore should result in correction in plasma chitotriosidase activity level and prophylactic therapy in prevention of the increase in plasma enzyme level. Indeed, concomittantly with clinical improvement plasma chitotriosidase activity levels decrease in Gaucher patients upon chronic intravenous administration of a glucocerebrosidase preparation, so called enzyme therapy [2]. The effect of enzyme therapy on plasma chitotriosidase was monitored for a very large number of Gaucher patients. FIG. 11 shows for example the plasma chitotriosidase levels in a large number of Gaucher patients receiving therapy for 10 months with different glucocerebrosidase dosing regimens. In those patients in which chitotriosidase levels did not respond poor clinical improvements were noted, often resulting in an increase of glucocerebrosidase dosage.

Provided information on chitotriosidase genotype staus is available, measurement of plasma chitotriosidase activity can be exploited for diagnosis of Gaucher disease, early detection of onset of the disorder and monitoring of therapy and subsequent optimalisation of the treatment.

In principle, plasma chitotriosidase levels should be a sensitive guideline to analyse the efficacy of any therapeutic intervention for Gaucher disease that aims to remove and/or prevent formation of storage cells.

EXAMPLE 2

Atherosclerosis: Detection of Foam Cells

Atherosclerosis is the pathological process in the vessel wall which eventually results in obstruction of blood flow [14]. The process involves infiltration and activation of lipid-laden macrophages ('foam cells') in the vessel wall. We hypothesized that in analogy to Gaucher disease chitotriosidase may be useful for monitoring of atherosclerosis.

1. Detection of Foam Cells

In Situ Hybridisation

As can be seen in FIG. 12, in situ hybridization revealed that chitotriosidase mRNA is present in the foam cells in atherosclerotic vessel walls. The in situ hybridization was performed as described earlier [15]. The sections were pretreated with proteinase K, refixed in paraformaldehyde and treated with acetic anhydride. Hybridizations were performed with a chitotriosidase probe of 199 nt (bp 970–1168) overnight, followed by a high stringency wash. After RNase A digestion and subsequent washings the material was dehydrated and autoradiographic emulsion was applied. Slides were developed after exposure of 3 days to 2 weeks, fixed and counterstained with haematoxylin eosin.

Enzyme Activity Measurement

Chitotriosidase activity levels were also determined in vessel wall material. In normal vessels the activity ranged from 0.5–2.1 nmol/h/mg (mean: 1.2; n=5) and in age-matched, corresponding atherosclerotic vascular material the activity ranged from 4.9–27.4 nmol/h/mg (mean: 16.4; n=5). No statistically significant elevation in steady state plasma chitotriosidase activity level could be demonstrated in relation to atherosclerosis, although the levels in plasma samples of patients with familial hypercholesterolemia tended to be on average 3-fold higher than in age-matched controls.

2. Diagnosis and (Preventive) Treatment

Chitotriosidase monitoring, for example in plasma, should be useful in monitoring the presence of atherosclerotic foam cells in individuals, especially those with a genetic defect that increases the risk for developing atherosclerosis. This could be employed for diagnostic reasons as well as to monitor the efficacy of (preventive) treatment. Again, information on the chitotriosidase genotype of a monitored individual would be essential for optimal interpretation of the enzyme activity data.

EXAMPLE 3

Sarcoidosis: Diagnosis and Therapy

Sarcoidosis is a disease of unknown etiology in which activated mononuclear phagocytes and T-lymphocytes are involved in formation of granulomas [16]. In sarcoidosis, granulomas develop in a variety of organs, most commonly the lungs, lymph nodes, bone, nervous tissue and skin. Activity of sarcoidosis has been defined by clinical features, accompanied by elevated levels of several plasma factors that are usually found in association with activated macrophages or T-lymphocytes [17]. Macrophage associated factors include angiotensin converting enzyme (ACE), lysozyme, sCD14, calcitrol, neopterin and sTNF receptors [18,19]. ACE determination is the most widely used laboratory test for sarcoidosis. However, ACE values have an estimated sensitivity of only 57% [20]. Especially in the first months of acute disease, ACE levels may be normal.

Diagnosis

The diagnostic value of chitotriosidase for sarcoidosis was investigated. As can be seen in FIG. 13, patients with sarcoidosis show elevated plasma chitotriosidase activity levels. The increase is much more spectacular as that in corresponding ACE levels (see FIG. 14).

The levels of ACE were elevated in 28 of 32 patients (median 90/U/l, range 26–282 U/l; normal range 18–55 U/l). Chitotriosidase was not deficient in any of the patients and elevated in all (median 577 nmol/ml. h, range 74–3032 nmol/ml. h, normal range <70 nmol/ml. h).

After completion of our study we did observe one sarcoidosis patient with chitotriosidase-deficiency.

The extent of elevation in plasma chitotriosidase seems to correlate with severity of disease manifestation, as can be seen in FIG. 13. We have been able to demonstrate by in situ hybridisation that the abnormal macrophages (epitheloid cells) in bronchoalveolar lavage fluid (BALF) of sarcoidosis patients contain large amounts of chitotriosidase RNA. Moreover, BALF of sarcoidosis patients shows high levels of chitotriosidase activity: control median concentration was 0.54 nmol/ml. h (range 0.32–1.67) and the calculated epithelial lining fluid (ELF) value was 53.2 nmol/ml. h (range 17.6–123.9). In the sarcoidosis patients the median concentration was 49.4 nmol/ml. h (range 0.72–468.9) for BALF and 1497.5 nmol/ml. h (range 67.3–33438) for ELF.

The measurement of plasma chitotriosidase activity, in combination with determination of chitotriosidase genotype, allows sensitive detection of clinical manifestation of sarcoidosis. Importantly, clear increases in plasma chitotriosidase were not observed in plasma of patients suffering from lymphomas (n=24) and leprosy (n=5). Chitotriosidase levels in plasma of untreated patients with pulmonary tuberculosis were slightly elevated in 7 of 12 patients (median 78.7 nmol/ml. h, range 8.2–147 nmol/ml. h). As compared to patients with sarcoidosis these levels were significantly lower. Thus, the relative simple and convenient chitotriosidase determination is extremely useful in the differential diagnosis of sarcoidosis.

Therapy

Sarcoidosis is treated by administration of corticosteroids. Determination of optimal drug dosage is critical but unfortunately also complicated. It was studied whether plasma chitotriosidase levels change upon treatment. FIG. 15 shows the chitotriosidase activity in a patient that received orally 25 mg of prednisone. This led to a marked reduction in plasma chitotriosidase activity. However, tapering of the dose to 5 mg per day after 17 weeks was followed by recurrence of disease activity while chitotriosidase activity increment preceeded the worsening of symptoms. FIG. 16 shows another example of a patient that was treated with corticosteroid pulse therapy (1000 mg methylprednisone for three days every 2 weeks). His chitotriosidase level before the initiation of treatment was very high, and it rapidly declined after the institution of corticosteroids. This was accompanied by marked clinical improvement.

The findings suggest that plasma chitotriosidase is an extremely useful guideline for diagnosis and optimalisation of anti-inflammatory treatement of sarcoidosis.

EXAMPLE 4

Multiple Sclerosis: Diagnosis and Therapy

Multiple sclerosis (MS) is a presumed T-cell mediated Th1 type autoimmune disease. In the pathophysiology of multiple sclerosis (MS) an important role is envisioned for activated T-lymphocytes and macrophages (see, e.g., ref. 19). It is generally thought that macrophages and resident brain microglia are agents of the demyelination that occurs in MS.

Chitotriosidase activity was determined in plasma and cerebral spine fluid (CSF) of MS patients. As shown in Table 3, in CSF of patients, but not in plasma, chitotriosidase activity is clearly elevated in relation to manifestation of MS. In a MS patient receiving recombinant beta-1B interferon treatment a concomitant 10-fold reduction in CSF chitotriosidase was noted by us.

These findings indicate that chitotriosidase measurement is useful to assess the presence of activated phagocytes in the brain of MS patients and correction therein following treatment. There is presently particularly a great need for reliable methods that will allow assessment of disease activity in MS patients during treatment.

EXAMPLE 5

Arthritis

Arthritis is characterized by inflammation of joints and an important role for activated phagocytes in the pathophysiology is generally assumed.

We investigated chitotriosidase activity in plasma and synovial fluid samples of patients with arthritis. As can be seen in Table 4, in arthritis plasma chitotriosidase activities tend to be above the normal value. In plasma of some patients very high levels have been observed, exceeding 1000 nmol/h/ml. In synovial fluid of arthritis cases a very high enzyme activity is demonstrable. The efficacy of anti-inflammatory treatment that aims to de-activate phagocytes in arthritis patients can be determined by analysis of chitotriosidase levels. Again, insight in the chitotriosidase genotype is essential for the interpretation of the results.

EXAMPLE 6

Crohn Disease

Crohn disease (enteritis regionalis) is characterized by chronic granulomatous inflammation of the duodenum and colon. Activated T-lymphocytes and a Thb 1-like profile of cytokine production are responsible for macrophage activation and release of anti-inflammatory cytokines, toxic oxygen metabolites and nitric oxide which maintain the intestinal Th1-type response. Chitotriosidase activities in untreated patients with active Crohn disease (n=5) were slightly (mean: 3.2 fold) elevated above the normal value. High chitotriosidase activity was detected in intestinal biopsies of a Crohn disease patient, being more than 20 fold that in corresponding control material.

The findings suggest that the sequential measurement of plasma chitotriosidase might represent a non-invasive method to assess Crohn disease activity and response to anti-inflammatory treatment.

EXAMPLE 7

Neutrophil Activation

To test the potential of chitotriosidase as a marker for the release of specific granules of neutrophils, we examined samples obtained in earlier studies in which granulocyte colony stimulating factor (G-CSF) or granulocyte-macrophage colony stimulating factor (GM-CSF) were administered to healthy volunteers [21,22]. In these experiments it was previously shown that degranulation of the specific granules of neutrophils occurs. As shown in FIG. 17, neutrophils release their specific granule content after 2 hours after G-CSF injection, as detectable by the appearance of lactoferrin in the circulation. Parallel increases in serum chitotriosidase levels are found. The increase in lactoferrin and chitotriosidase is not due to an increase in neutrophil cell number, because these levels peak later in time, after about 12 hours. A second peak in lactoferrin and chitotriosidase levels is seen after 6 to days after G-CSF injection. This is most likely caused by the turnover of the large amount of cells formed after G-CSF induction. Administration of GM-CSF gave similar results (not shown) except for the second peak which was not present.

The findings suggest that plasma chitotriosidase may be used to detect activation (that is, degranulation) of neutrophils, as for example induced with G-CSF or GM-CSF.

REFERENCES

1. Beutler E., Grabowski G. Gaucher disease. In: Scriver, C. R., Sly, W. S., Valle, D., ed. The metabolic basis of inherited disease. New York: McGraw-Hill, New York, 1995: 2641–2670.

2. Hollak C. E. M., van Weely, S., van Oers, M. H. J., Aerts, J. M. F. G. Marked elevation of plasma chitotriosidase activity. A novel hallmark of Gaucher disease. J. Clin. Invest. 1994; 93: 1288–1292.

3. Sahai, A. S., Manocha, M. S. Chitinases of fungi and plants: their involvement in morphogenesis and host-parasite interaction. FEMS Microbiology Reviews 1993; 11: 317–338.

4. Kauffman, C. A., Hedderwick, S. Opportunistic fungal infections: filamentous fungi and cryptococcocis. Geriatrics 1997; 52: 40–49.

5. Boot, R. G., Renkema, G. H., Strijland, A. et al. Cloning of a cDNA encoding chitotriosidase, a human chitinase produced by macrophages. J. Biol. Chem. 1995; 270: 26252–26256.

6. Renkema, G. H., Boot, R. G., Muijsers, A. O. et al. Purification and characterization of human chitotriosidase, a novel member of the chitinase family of proteins. J. Biol. Chem. 1995; 270: 2198–2202.

7. Renkema, G. H., Boot, R. G., Au, F. L. et al. Chitotriosidase, a chitinase, and the 39 kDa human cartilage glycoprotein, a chitin-binding lectin are homologues of family of glycosyl-hydrolases secreted by human macrophages. Eur. J. Biochem. 1998; 251: 504–509.

8. Hakala, B. E., White, C., Recklies, A. D. Human cartilage gp-39, a major secretory product of articular chondrocytes and synovial cells. J. Biol. Chem. 1995; 268: 25803–25810.

9. Verheijden, G. F. M., Rijnders, A. W. M., Bos, E. et al. Human cartilage glycoprotein 39 as a candidate autoantigen in rheumatoid arthritis. Arthritis & Rheumatism 1997; 40: 1115–1125.

10. Renkema, G. H., Boot, R. G., Strijland, A. et al. Synthesis, sorting and processing into distinct isoforms of human macrophage chitotriosidase. Eur. J. Biochem. 1997; 244: 279–285.

11. Escott, G. M., Adams, D. J. Chitinase activity in human serum and leukocytes. Infect. Immun. 1995; 63: 4770–4773.

12. Kuijpers, T. W., Tool, A. T., van der Schoot, C. E., et al. Membrane surface antigen expression on neutrophils: a reappraisal of the use of surface makers for neutrophil activation. Blood 1991; 78: 1105–1111.

13. Borregaard, N. Current concepts about neutrophil granule physiology. Curr. Opin. Hematol. 1996; 3: 11–18.

14. Ross, R. The pathogenesis of atherosclerosis: a perspective for the 1990s. Nature 1993; 362: 801–809.

15. Wilkinson, D., Green, J. In situ hybridization and the three-dimensional reconstruction of serial sections. In: Postimplantation mammalian embryos. Copp, A. J., Crockfort, D. L., eds. Oxford University Press, 1990: 155–171.

16. Semenzato, G., Agostino, C. Immunology of sarcoidosis. In: Schwarz, M. I., King, T. E., eds. Interstitual lung disease. 2nd ed. St. Louis: 1993: 127–158.

17. Consensus conference: activity of sarcoidosis. Third WASOG meeting. Los Angeles, USA: Eur. Respir. J., 1994, 1993: 624–627.

18. Sharma, O. P. Markers of sarcoidosis activity. Chest 1986; 90: 471–473.

19. Janzen, R. W. C. New realizations of therapy of multiple sclerosis with beta-interferone. Fortschritt und Fortbildung in der Medizin 1997; 20: 441–450.

20. Romagnani, P., Annunziato, F., Baccari, M. C., Parrochi, P. T-cells and cytokines in Crohn's disease. Curr. Opin. Immunol. 1997; 9: 793–721.

21. De Haas, M., Kerst, J. M., van der Schoot, J. et al. Granulocyte colony stimulating factor administration to healthy volunteers: analysis of the immediate activating effects on circulating neutrophils. Blood 1994; 84: 3885–3894.

22. Van Pelt, L. J., Huisman, M. V., Weening, R. S. et al. A single dose of granulocyte-macrophage colony-stimulating factor induces systemic interleukin-8 release and neutrophil activation in healthy volunteers. Blood 1996; 87: 5305–5313.

TABLE 1

Chitotriosidase activity in plasma and leukocytes. Chitotriosidase activity was measured in plasma samples and leukocyte extracts with the 4MU-chitotrioside substrate, as described in Materials and Methods. Residual enzyme activity present in the samples from chitotriosidase-deficient persons was resistant to incubation with the anti-(chitotriosidase)antiserum.

|  |  | plasma (nmol/ml · h) | leukocytes (nmol/ml · mg protein) |
|---|---|---|---|
| Control subjects |  |  |  |
| not deficient | n | 50 | 50 |
|  | mean | 22.4 | 424 |
|  | range | 5.1–75.6 | 22–960 |
| deficient | n | 2 |  |
|  |  | 3.3; 4.1 | 11; 18 |
| Gaucher patients |  |  |  |
| not deficient | n | 30 | 16 |
|  | mean | 16.485 | 398 |
|  | range | 2,949–55,679 | 64–812 |

TABLE 1-continued

Chitotriosidase activity in plasma and leukocytes. Chitotriosidase activity was measured in plasma samples and leukocyte extracts with the 4MU-chitotrioside substrate, as described in Materials and Methods. Residual enzyme activity present in the samples from chitotriosidase-deficient persons was resistant to incubation with the anti-(chitotriosidase)antiserum.

|  |  | plasma (nmol/ml · h) | leukocytes (nmol/ml · mg protein) |
|---|---|---|---|
| deficient | n | 2 | 2 |
|  |  | 2.1; 3.1 | 9; 13 |

TABLE 2

Chitinase activity in neutrophils. Chitinase activity was measured in neutrophil extracts as described in Materials and Methods. Neutrophils were taken either from control persons and measured with or without pre-treatment with an anti-(chitotriosidase)antiserum, or from chitotriosidase-deficient individuals.

|  |  | Chitinase activity (nmol/ml · mg protein) |
|---|---|---|
| Control neutrophils | n | 4 |
|  | mean | 74.9 |
|  | range | 47.5–102 |
| After pre-treatment with anti-(chitotriosidase)antiserum | n | 4 |
|  | mean | 3.0 |
|  | range | 0.7–5.1 |
| Chitotriosidase-deficient neutrophils | n | 2 |
|  |  | 3.6; 4.9 |

TABLE 3

Chitotriosidase activity in plasma of arthritis patients. Activity is expressed in nmol/ml · h. Activity was determined as described earlier [2], with the exception that anti-chitotriosidase antiserum was employed to determine the true collaboration of chitotriosidase to the total hydrolysis of 4-methylumbelliferyl-chitotrioside.

|  | N | Mean | Range |
|---|---|---|---|
| Arthritis cases | 71 | 173 | 1–2264 |
| Control subjects | 50 | 23 | 5–76 |

TABLE 4

Chitotriosidase in cerebral spine fluid and plasma of patients with multiple sclerosis and X-linked adreno-leukodystrophy. Activities were determined as described in Table 3

|  | N | Mean | Range |
|---|---|---|---|
| A. Plasma chitotriosidase (in nmol/ml · h) | | | |
| Multiple Sclerosis patients | 15 | 53 | 13–127 |
| X-ALD patients | 17 | 38 | 14–130 |
| Control subjects | 50 | 23 | 1–76 |
| B. CSF chitotriosidase (in nmol/ml · h) | | | |
| Multiple sclerosis patients | 15 | 50 | 2–263 |
| X-ALD patients | 17 | 57 | 2–124 |
| Control subjects | 15 | 4 | 1–9 |

What is claimed is:

1. A method for determining the chitotriosidase genotype of an individual comprising distinguishing a mutant chitotriosidase gene from a wild type chitotriosidase gene by the presence of a duplication of 24 nucleotides in exon 10 in said mutant chitotriosidase gene.

2. The method of claim 1 wherein genomic DNA is examined to determine the presence of a wild type chitotriosidase gene, the presence of a mutant chitotriosidase gene, or both.

3. The method of claim 2 wherein said 24 nucleotides are from the codons coding for amino acids Nos. 350 to 358 of chitotriosidase.

4. The method of claim 3 wherein genomic DNA derived from said individual is subjected to nucleic acid amplification, using a first primer which comprises a nucleotide sequence complementary to a first part of the chitotriosidase gene and a second primer which comprises a nucleotide sequence complementary to a second part of the chitotriosidase gene, wherein said first and second primers are complementary to opposite strands of the DNA and enclose the region coding for amino acids Nos. 350 to 358 of chitotriosidase.

5. The method of claim 4 wherein said first primer comprises the nucleotide sequence 5'-AGCTATCTGAAGCAGAAG-3' (SEQ ID NO 1) and said second primer comprises the nucleotide sequence 5'-GGAGAAGCCGGCAAAGTC-3' (SEQ ID NO 2).

6. The method of claim 4 wherein said first primer comprises the nucleotide sequence 5'-TATCTGAAGCAGAAG-3' (SEQ ID NO 3) and said second primer comprises the nucleotide sequence 5'-GAAGCCGGCAAAGTC-3' (SEQ ID NO 4).

7. The method of claim 4 wherein said first primer comprises the nucleotide sequence 5'-CTCCCTGCACAGGTCAGC-3' (SEQ ID NO 5) and said second primer comprises the nucleotide sequence 5' GTATCGGCCCTGGTTGCA-3' (SEQ ID NO 10).

8. The method of claim 4 wherein amplified nucleic acid is subjected to a technique which separates nucleic acid molecules on the basis of length, to determine the presence of wild type chitotriosidase derived amplicons, the presence of mutant chitotriosidase derived amplicons, or both.

9. A method for determining the chitotriosidase genotype of an individual comprising distinguishing a mutant chitotriosidase RNA from a wild type chitotriosidase RNA by the absence in said mutant chitotriosidase RNA of 87 nucleotides coding for amino acids Nos. 344 to 372 of chitotriosidase.

10. The method of claim 9 wherein RNA derived from said individual is subjected to nucleic acid amplification using a first primer which comprises a nucleotide sequence complementary to a first part of the chitotriosidase RNA and a second primer which comprises a nucleotide sequence corresponding to a second part of the chitotriosidase RNA, and the primers enclose the region coding for amino acids Nos. 344 to 372 of chitotriosidase.

11. The method of claim 10 wherein one of said primers comprises the nucleotide sequence 5' TCAGTTCCTGCCGTAGCGTC 3' (SEQ ID NO 11) and the other primer comprises the nucleotide sequence 5' TACATCTTCCGGGACAACCA 3' (SEQ ID NO 12).

12. The method of claim 10 wherein amplified nucleic acid is subjected to a technique which separates nucleic acid molecules on the basis of length, to determine the presence of wild type chitotriosidase derived amplicons, the presence of mutant chitotriosidase derived amplicons, or both.

13. A method for determining the chitotriosidase genotype of an individual comprising distinguishing a mutant chitotriosidase RNA derived cDNA from a wild type chitotriosidase RNA derived cDNA by the absence in said mutant chitotriosidase RNA derived cDNA of 87 nucleotides coding for amino acids Nos. 344 to 372 of chitotriosidase.

14. The method of claim 13 wherein cDNA derived from RNA derived from said individual is subjected to nucleic acid amplification using a first primer which comprises a nucleotide sequence complementary to a first part of the chitotriosidase cDNA and a second primer which comprises a nucleotide sequence complementary to a second part of the chitotriosidase cDNA, wherein said first and second primers are complementary to opposite strands of the cDNA and enclose the region coding for amino acids Nos. 344 to 372 of chitotriosidase.

15. The method of claim 15 wherein one of said primers comprises the nucleotide sequence 5' TCAGTTCCTGCCGTAGCGTC 3' (SEQ ID NO 11) and the other primer comprises the nucleotide sequence 5' TACATCTTCCGGGACAACCA 3' (SEQ ID NO 12).

16. The method of claim 14 wherein amplified nucleic acid is subjected to a technique which separates nucleic acid molecules on the basis of length, to determine the presence of wild type chitotriosidase derived amplicons, the presence of mutant chitotriosidase derived amplicons, or both.

17. A test kit for determining the chitotriosidase genotype of an individual, comprising means for isolating nucleic acid from said individual, means for amplifying a selected part of chitotriosidase-encoding nucleic acid, and means for analyzing amplified nucleic acid to distinguish wild type chitotriosidase nucleic acid from mutant chitotriosidase nucleic acid wherein said means for isolating nucleic acid is a means for isolating genomic DNA, said means for amplifying a selected part of chitotriosidase-encoding nucleic acid is a means for amplifying a selected part of chitotriosidase-encoding genomic DNA, and said means for analyzing amplified nucleic acid detects the presence of a duplication of 24 nucleotides from the codons coding for amino acids nos. 350–358 of chitotriosidase to distinguish mutant chitotriosidase nucleic acid which contains this duplication, from wild type chitotriosidase nucleic acid.

18. The test kit of claim 17 wherein said means for amplifying a selected part of chitotriosidase-encoding genomic DNA comprises PCR primers and optionally other PCR reagents, said PCR primers comprising a first primer which comprises a nucleotide sequence complementary to a first part of the chitotriosidase gene and a second primer which comprises a nucleotide sequence complementary to a second part of the chitotriosidase gene, wherein said first and second primers are complementary to opposite strands of the DNA and enclose the region coding for amino acids Nos. 350 to 358 of chitotriosidase.

19. A test kit for determining the chitotriosidase genotype of an individual, comprising means for isolating nucleic acid from said individual, means for amplifying a selected part of chitotriosidase-encoding nucleic acid, and means for analyzing amplified nucleic acid to distinguish wild type chitotriosidase nucleic acid from mutant chitotriosidase nucleic acid wherein said means for isolating nucleic acid is a means for isolating mRNA, said means for amplifying a selected part of chitotriosidase-encoding nucleic acid is a means for amplifying a selected part of chitotriosidase-encoding mRNA or mRNA-derived cDNA, and said means for analyzing amplified nucleic acid detects the absence of 87 nucleotide coding for amino acids nos. 344 to 372 of chitotriosidase to distinguish mutant chitotriosidase nucleic acid, in which these nucleotides are missing, from wild type chitotriosidase nucleic acid.

20. The test kit of claim 19 wherein said means for amplifying a selected part of chitotriosidase-encoding mRNA or mRNA-derived cDNA comprises PCR, RT-PCR or NASBA primers and optionally other PCR, RT-PCR or NASBA reagents, said primers comprising a first primer which comprises a nucleotide sequence complementary to a first part of the chitotriosidase RNA and a second primer which comprises a nucleotide sequence complementary to the complement of a second part of the chitotriosidase RNA, and the primers enclose the region coding for amino acids Nos. 344 to 372 of chitotriosidase.

* * * * *

UNITED STATES PATENT AND TRADEMARK OFFICE
CERTIFICATE OF CORRECTION

PATENT NO. : 6,221,591 B1  
DATED : April 24, 2001  
INVENTOR(S) : Johannes M.F.G Aerts Page 1 of 1

It is certified that error appears in the above-identified patent and that said Letters Patent is hereby corrected as shown below:

<u>Title page,</u>
Item [74], now reads "Hoffman & Baron, LLP" should read -- Hoffmann & Baron, LLP --;

Signed and Sealed this

Second Day of April, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.   : 6,221,591 B1
DATED        : April 24, 2001
INVENTOR(S)  : Johannes M.F.G. Aerts It is certified that error appears in the above-identified patent and that said Letters Patent is hereby corrected as shown below:

Column 3,
Line 47, now read "shown. The arrows indicate the primers..."; should read -- shown (SEQ ID NO. 13, SEQ ID NO. 14). The arrows indicate the primers... --.
Line 49, now reads "CDNA" is depicted."; should read -- CDNA is depicted (SEQ ID NO. 15, SEQ ID NO. 16. --;
Lines 53 and 54, now reads "the normal gene. The arrows"; should read -- the normal gene (SEQ ID NO. 17, SEQ ID NO. 19. The arrows... --.
Line 57, now reads "the mutant gene. The mutant gene..."; should read -- the mutant gene (SEQ ID NO. 18, SEQ ID NO. 20. The mutant gene..." --.

Column 8,
Line 7, now reads "GCG, GTC 3' AND 5' GAA..."; should read -- GCG, GTC 3' (SEQ ID NO. 6) and 5' GAA... --.
Line 7, now reads "GAG AGC 3' [5]."; should read -- GAG AGC 3' (SEQ ID NO. 7) [5]. --

Column 9,
Line 52, now reads CAG 3'. Protected fragments..."; should read -- CAG 3' (SEQ ID NO. 8). Protected fragments... --.
Line 63, now reads "GCC T 3' and normal primer 5' GGA"; should read -- GCC T 3'(SEQ ID NO. 9) and normal primer 5' GGA --.
Line 64, now reads "GTC 3' will generate PCR fragments"; should read -- GTC 3' (SEQ ID NO. 2) will generate PCR fragments --.

Signed and Sealed this

Twenty-seventh Day of August, 2002

*Attest:*

*Attesting Officer*

JAMES E. ROGAN
*Director of the United States Patent and Trademark Office*

SEQUENCE LISTING

<160> NUMBER OF SEQ ID NOS: 20

<210> SEQ ID NO 1
<211> LENGTH: 18
<212> TYPE: DNA
<213> ORGANISM: Homo sapiens

<400> SEQUENCE: 1
agctatctga agcagaag                                                                 18

<210> SEQ ID NO 2
<211> LENGTH: 18
<212> TYPE: DNA
<213> ORGANISM: Homo sapiens

<400> SEQUENCE: 2
ggagaagccg gcaaagtc                                                                 18

<210> SEQ ID NO 3
<211> LENGTH: 15
<212> TYPE: DNA
<213> ORGANISM: Homo sapiens

<400> SEQUENCE: 3
tatctgaagc agaag                                                                    15

<210> SEQ ID NO 4
<211> LENGTH: 15
<212> TYPE: DNA
<213> ORGANISM: Homo sapiens

<400> SEQUENCE: 4
gaagccggca aagtc                                                                    15

<210> SEQ ID NO 5
<211> LENGTH: 18
<212> TYPE: DNA
<213> ORGANISM: Homo sapiens

<400> SEQUENCE: 5
ctccctgcac aggtcagc                                                                 18

<210> SEQ ID NO 6
<211> LENGTH: 18
<212> TYPE: DNA
<213> ORGANISM: Homo sapiens

<400> SEQUENCE: 6
ctgcatcatg gtgcggtc                                                                 18

<210> SEQ ID NO 7
<211> LENGTH: 18
<212> TYPE: DNA
<213> ORGANISM: Homo sapiens

<400> SEQUENCE: 7
gaaggcaagg ctgagagc                                                                 18

<210> SEQ ID NO 8
<211> LENGTH: 147
<212> TYPE: DNA
<213> ORGANISM: Homo sapiens -continued

<400> SEQUENCE: 8
tacatcttcc gggacaacca gtgggtcggc tttgatgatg tcgagagctt caaaaccaag    60
gtcagctatc tgaagcagaa gggactgggc ggggccatgg tctgggcact ggacttagat   120
gactttgccg gcttctcctg caaccag                                       147

<210> SEQ ID NO 9
<211> LENGTH: 16
<212> TYPE: DNA
<213> ORGANISM: Homo sapiens

<400> SEQUENCE: 9
ggcggggcca tggcct                                                    16

<210> SEQ ID NO 10
<211> LENGTH: 18
<212> TYPE: DNA
<213> ORGANISM: Homo sapiens

<400> SEQUENCE: 10
gtatcggccc tggttgca                                                  18

<210> SEQ ID NO 11
<211> LENGTH: 20
<212> TYPE: DNA
<213> ORGANISM: Homo sapiens

<400> SEQUENCE: 11
tcagttcctg ccgtagcgtc                                                20

<210> SEQ ID NO 12
<211> LENGTH: 20
<212> TYPE: DNA
<213> ORGANISM: Homo sapiens

<400> SEQUENCE: 12
tacatcttcc gggacaacca                                                20

<210> SEQ ID NO 13
<211> LENGTH: 105
<212> TYPE: DNA
<213> ORGANISM: Homo sapiens

<400> SEQUENCE: 13
aaaaccaagg tcagctatct gaagcagaag ggactgggcg gggccatggt ctgggcactg    60
gacttagatg actttgccgg cttctcctgc aaccagggcc gatac                   105

<210> SEQ ID NO 14
<211> LENGTH: 35
<212> TYPE: PRT
<213> ORGANISM: Homo sapiens

<400> SEQUENCE: 14

Lys Thr Lys Val Ser Tyr Leu Lys Gln Lys Gly Leu Gly Gly Ala Met
  1               5                  10                  15

Val Trp Ala Leu Asp Leu Asp Asp Phe Ala Gly Phe Ser Cys Asn Gln
                 20                  25                  30

Gly Arg Tyr
         35

```
<210> SEQ ID NO 15
<211> LENGTH: 18
<212> TYPE: DNA
<213> ORGANISM: Homo sapiens

<400> SEQUENCE: 15
aaaaccaagg gccgatac                                              18

<210> SEQ ID NO 16
<211> LENGTH: 6
<212> TYPE: PRT
<213> ORGANISM: Homo sapiens

<400> SEQUENCE: 16

Lys Thr Lys Gly Arg Tyr
 1               5

<210> SEQ ID NO 17
<211> LENGTH: 96
<212> TYPE: DNA
<213> ORGANISM: Homo sapiens

<400> SEQUENCE: 17
gtcagctatc tgaagcagaa gggactgggc ggggccatgg tctgggcact ggacttagat    60
gactttgccg gcttctcctg caaccagggc cgatac                              96

<210> SEQ ID NO 18
<211> LENGTH: 120
<212> TYPE: DNA
<213> ORGANISM: Homo sapiens

<400> SEQUENCE: 18
gtcagctatc tgaagcagaa gggactgggc ggggccatgg tctagggact gggcggggcc    60
atggtctggg cactggactt agatgacttt gccggcttct cctgcaacca gggccgatac   120

<210> SEQ ID NO 19
<211> LENGTH: 108
<212> TYPE: DNA
<213> ORGANISM: Homo sapiens

<400> SEQUENCE: 19
ctccctgcac aggtcagcta tctgaagcag aagggactgg gcggggccat ggtctgggca    60
ctggacttag atgactttgc cggcttctcc tgcaaccagg gccgatac                108

<210> SEQ ID NO 20
<211> LENGTH: 132
<212> TYPE: DNA
<213> ORGANISM: Homo sapiens

<400> SEQUENCE: 20
ctccctgcac aggtcagcta tctgaagcag aagggactgg gcggggccat ggtctaggga    60
ctgggcgggg ccatggtctg gcactggac ttagatgact ttgccggctt ctcctgcaac    120
cagggccgat ac                                                       132
```